(12) United States Patent
Norimine et al.

(10) Patent No.: US 6,774,383 B2
(45) Date of Patent: Aug. 10, 2004

(54) PARTICLE THERAPY SYSTEM

(75) Inventors: Tetsuro Norimine, Hitachi (JP);
Masumi Umezawa, Hitachi (JP);
Kazuo Hiramoto, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/395,144

(22) Filed: Mar. 25, 2003

(65) Prior Publication Data

US 2003/0183779 A1 Oct. 2, 2003

(30) Foreign Application Priority Data

Mar. 26, 2002 (JP) ........................................ 2002-085862

(51) Int. Cl.[7] .......................... H05H 13/04; A61N 5/10; G21G 1/10
(52) U.S. Cl. ............................... 250/505.1; 250/492.3; 315/503; 315/507; 378/65
(58) Field of Search .......................... 250/505.1, 492.3; 315/503, 507; 378/65

(56) References Cited

U.S. PATENT DOCUMENTS

| 5,698,954 A | * | 12/1997 | Hirota et al. ................ 315/503 |
| 5,895,926 A | * | 4/1999 | Britton et al. ............ 250/492.3 |
| 5,986,274 A | * | 11/1999 | Akiyama et al. ......... 250/492.3 |
| 6,265,837 B1 | * | 7/2001 | Akiyama et al. ........... 315/503 |

FOREIGN PATENT DOCUMENTS

| EP | 0 986 070 A | 3/2000 |
| EP | 1 045 399 A | 10/2000 |
| JP | 2001 210498 A | 8/2001 |
| WO | WO 02/063638 A1 | 8/2002 |

* cited by examiner

Primary Examiner—Nikita Wells
(74) Attorney, Agent, or Firm—Dickstein Shapiro Morin & Oshinsky LLP

(57) ABSTRACT

A particle therapy system is provided which can simply and quickly correct a beam orbit. In a particle therapy system provided with an irradiation facility comprising a first beam transport system for receiving a beam and transporting the beam to the patient side, and an irradiation nozzle for forming an irradiation field of the beam, the particle therapy system comprises first beam position monitors for detecting a position upstream of the irradiation nozzle at which the beam passes, second beam position monitors for detecting a position downstream of the irradiation nozzle at which the charged-particle beam passes, and first and second steering magnets. Correction bending amounts for causing the beam to be coincident with a predetermined orbit after the correction are determined in accordance with detected results from the first and second beam position monitors, and first and second steering magnets are excited under control so that the determined correction bending amounts are obtained.

19 Claims, 12 Drawing Sheets

PARTICLE THERAPY SYSTEM

BACKGROUND OF THE INVENTION

1. Field of the Invention

The present invention relates to a particle therapy system for treating diseases, such as cancer and tumor, by using a charged-particle beam.

2. Description of the Related Art

In a therapy system for treating diseases, such as cancer and tumor, by irradiating protons or heavy ions, as charged particles, to a diseased area of a patient, a charged-particle beam accelerated by an accelerator, e.g., a synchrotron, is incident upon a transport means provided in a rotating (or stationary) irradiation facility, and is then introduced to an irradiation field forming apparatus. After shaping an irradiation field in match with the shape of the diseased area by the irradiation field forming apparatus, the charged-particle beam is irradiated to the diseased area of the patient lying on a patient bed that is installed below the irradiation field forming apparatus.

One example of such a therapy system is disclosed in, e.g., Japanese Unexamined Patent Application Publication No. 2001-210498. In this prior-art system, bending magnets for bending a beam direction and quadrupole magnets for adjusting a beam size are included in transport means that are provided in a high energy beam transport (HEBT) system from a synchrotron to a rotating irradiation facility and in the rotating irradiation facility. An irradiation unit serving as the irradiation field forming apparatus is provided downstream of the transport means.

As methods for forming an irradiation field by the irradiation field forming apparatus, there are conventionally known a method of enlarging a beam by using scatterers, and a beam scanning method of scanning a beam and making an amount of irradiated beam uniform through superimposition of the scanned beams.

With the method using scatterers, the beam is enlarged by employing, for example, a first scatterer made of one kind of metal and a second scatterer made of two kinds of metals having different densities. Then, beam intensity distributions resulting from those two scatterers are superimposed with each other to realize a uniform beam intensity distribution. To that end, the beam must be passed in a state in which a beam center (beam axis) coincides with a center axis of each scatterer (design orbit of the irradiation field forming apparatus), so that the beam intensity distribution resulting from each scatterer becomes symmetric about the axis.

On the other hand, with the beam scanning method, the beam is introduced to propagate in the z-direction, and varying currents are supplied to an x-direction scanning magnet and a y-direction scanning magnet to change magnetic fields generated by those magnets over time so that the beam is scanned in the x-direction and the y-direction. For example, by setting the number of scans in the x-direction per unit time to a relatively large value and the number of scans in the y-direction per unit time to a relatively small value, the irradiation field having a desired form can be formed. In this method, if the beam enters the scanning magnets in a state in which the beam axis is shifted from the design orbit, the irradiation zone is deviated from the diseased area and a uniform amount of the irradiated beam is not realized through superimposition of the scanned beams. For that reason, the beam must be introduced so as to pass predetermined positions (=design orbit of the irradiation field forming apparatus) of the two scanning magnets.

As described above, when introducing the beam from the transport means to the irradiation field forming apparatus, the beam axis is required to coincide with the design orbit of the irradiation field forming apparatus irrespective of which one of the irradiation field forming methods is employed. To that end, various components of the transport means are generally designed and arranged so that, when transporting the beam to the irradiation field forming apparatus, the beam axis is finally coincident with the design orbit of the irradiation field forming apparatus.

In practice, however, it is unavoidable that the direction of the beam axis is slightly deviated because of shape or dimension tolerances of the components of the transport means and layout or assembly errors (referred to also as "alignment errors" hereinafter). In the above-described prior-art therapy system, therefore, steering magnets are provided in a low energy beam transport (LEBT) system and the high energy beam transport (HEBT) system. Stated otherwise, though not clearly disclosed in the above-described prior art, it is usual that, assuming one direction (e.g., bending direction by the bending magnets) to be the x-direction and a direction perpendicular to the one direction (e.g., direction perpendicular to the bending direction by the bending magnets) to be the y-direction, two steering magnets for the x-direction are employed to adjust the displacement and the gradient of the beam in a plane containing the x-axis, and two steering magnets for the y-direction are also employed to adjust the displacement and the gradient of the beam in a plane containing the y-axis. With those steering magnets, the beam axis is made coincident with the design orbit of the irradiation field forming apparatus.

More specifically, the orbit is corrected through steps of, for example, installing two x-direction and y-direction monitors in the high energy beam transport (HEBT) system to detect respective displacements and gradients of the beam, and exciting the two steering magnets for each of the x-direction and the y-direction. When carrying out the operation of correcting the beam orbit, because it is unknown how large the alignment errors are, an operator has been usually required to perform adjustment on a trial-and-error basis, i.e., to manually increase or decrease bending amounts (referred to also as "kick amounts" hereinafter) of the x-direction and y-direction steering magnets as appropriate and to perform manual adjustment to coincide the beam position with the design orbit while looking at a tendency of resulting changes in the beam displacement and gradient.

Thus, in the conventional therapy system, because the beam orbit has been corrected on a trial-and-error basis while manually changing the kick amount of each steering, magnet, a lot of labor and time have been required to carry out the operation of correcting the beam orbit.

Particularly, in the so-called rotating irradiation facility, as employed in the above-described prior art, wherein a rotating irradiator including the transport means and the irradiation field forming apparatus is rotatably installed about an axis of rotation so that the beam can be irradiated from a proper angular position in match with the position and condition of the diseased area, the amounts of flexures, deformations, etc. of various components caused by their own weights change depending on the rotational angle of the irradiator, and the alignment errors also change depending on the rotational angle. Hence, the operation of correcting the beam orbit must be repeated on a trial-and-error basis whenever the rotational angle of the rotating irradiator (rotating irradiation facility) is changed, thus resulting in a very troublesome operation.

SUMMARY OF THE INVENTION

Accordingly, it is an object of the present invention to provide a particle therapy system, which can simply and quickly correct a beam orbit.

(1) To achieve the above object, the present invention provides a particle therapy system comprising an accelerator for accelerating a charged-particle beam to a set level of energy, and a rotating irradiation facility for irradiating the charged-particle beam extracted from the accelerator, the irradiation facility comprising a first beam transport unit for transporting the charged-particle beam extracted from the accelerator, and an irradiation field forming unit for forming an irradiation field of the charged-particle beam transported by the first beam transport unit, wherein the particle therapy system further comprises a first beam position detecting unit arranged along an orbit of the charged-particle beam downstream of a most downstream one of magnets provided in the first beam transport unit, and detecting a position at which the charged-particle beam passes; a second beam position detecting unit arranged along the orbit of the charged-particle beam downstream of the first beam position detecting unit, and detecting a position at which the charged-particle beam passes; a first steering magnet and a second steering magnet both provided in the first beam transport unit upstream of the first beam position detecting unit; a first displacement amount computing unit for determining respective first displacement amounts, by which the position of the charged-particle beam is to be displaced by the first and second steering magnets, in accordance with detected signals outputted from the first and second beam position detecting units; and a first control unit for controlling respective excitation currents of the first and second steering magnets in accordance with the respective first displacement amounts.

With the present invention having the above features, the position at which the charged-particle beam passes is detected by the first and second beam position detecting units downstream of the most downstream one of the magnets provided in the first beam transport unit, the first displacement amount computing unit determines, in accordance with the detected signals outputted from the first and second beam position detecting units, first displacement amounts (e.g., respective first displacement amounts by which the position of the charged-particle beam is to be displaced by the first and second steering magnets on the basis of approximation models using transfer matrices of various transport elements), and the first control unit controls respective excitation currents of the first and second steering magnets in accordance with the first displacement amounts. Hence, the position of the charged-particle beam can be displaced, as required, to come within a set range (e.g., a design orbit of the irradiation field forming unit). As a result, the orbit correction can be more simply and quickly performed, while greatly reducing the required labor and time, as compared with the conventional system in which the beam orbit is corrected on a trial-and-error basis by manually changing respective kick amounts of steering magnets.

(2) In above (1), preferably, the irradiation field forming unit includes a first scatterer and a second scatterer arranged downstream of the first scatterer, and the first beam position detecting unit is arranged upstream of the second scatterer.

(3) In above (1), preferably, the irradiation field forming unit includes a beam scanning unit for scanning the charged-particle beam, and the first beam position detecting unit is arranged upstream of the beam scanning unit.

(4)(5)(6) In any one of above (1) to (3), preferably, the first displacement amount computing unit determines the first displacement amounts in accordance with the detected signals outputted from the first and second beam position detecting units so that the position of the charged-particle beam comes within a set orbit in the irradiation field forming unit.

(7)(8) In above (1) or (6), preferably, the first displacement amount computing unit determines the first displacement amounts on the basis of approximation models using a plurality of transfer matrices representing respective transport characteristics of various transport elements of the first beam transport unit, which include at least the first and second steering magnets.

(9)(10) In above (1) or (4), preferably, at least one of the first and second steering magnets displace the charged-particle beam in one direction and displace the charged-particle beam in an other direction perpendicular to the one direction.

With that feature, the number of the steering magnets used can be reduced and an installation space can be reduced, thus resulting in a smaller size of the irradiation facility.

(11) Also, to achieve the above object, the present invention provides a particle therapy system comprising an accelerator for accelerating a charged-particle beam to a set level of energy, a rotating irradiation facility for irradiating the charged-particle beam extracted from the accelerator, and a second beam transport unit for transporting the charged-particle beam extracted from the accelerator to the irradiation facility, wherein the particle therapy system further comprises a third beam position detecting unit for detecting a position in the second beam transport unit at which the charged-particle beam passes; a fourth beam position detecting unit for detecting, downstream of the third beam position detecting unit, a position in the second beam transport unit at which the charged-particle beam passes; a third steering magnet and a fourth steering magnet both provided in the second beam transport unit upstream of the third beam position detecting unit; a second displacement amount computing unit for determining second displacement amounts, by which the position of the charged-particle beam is to be displaced by the third and fourth steering magnets, in accordance with detected signals outputted from the third and fourth beam position detecting units; and a second control unit for controlling respective excitation currents of the third and fourth steering magnets in accordance with the respective second displacement amounts.

With the present invention having the above features, the position at which the charged-particle beam passes is detected by the third and fourth beam position detecting units downstream of the most downstream one of the magnets provided in the second beam transport unit, the second displacement amount computing unit determines, in accordance detected the signals outputted from the third and fourth beam position detecting units, second displacement amounts (e.g., respective second displacement amounts by which the position of the charged-particle beam is to be displaced by the first and second steering magnets on the basis of approximation models using transfer matrices of various transport elements), and the second control unit controls respective excitation currents of the third and fourth steering magnets in accordance with the second displacement amounts. Hence, the position of the charged-particle beam can be displaced, as required, to come within a set range (e.g., a design orbit of the irradiation field forming unit). As a result, the orbit correction can be more simply and quickly performed, while greatly reducing the required labor and time, as compared with the conventional system in which the beam orbit is corrected on a trial-and-error basis by manually changing respective kick amounts of steering magnets.

(12) In above (11), preferably, the second displacement amount computing unit determines the second displacement amounts in accordance with the detected signals outputted from the third and fourth beam position detecting units so that the position of the charged-particle beam comes within a set orbit in the irradiation field forming unit.

(13)(14) In above (11) or (12), preferably, the second displacement amount computing unit determines the second displacement amounts on the basis of approximation models using a plurality of transfer matrices representing respective transport characteristics of various transport elements of the second beam transport unit, which include at least the third and fourth steering magnets.

(15)(16) In above (11) or (12), preferably, at least one of the third and fourth steering magnets displace the charged-particle beam in one direction and displace the charged-particle beam in an other direction perpendicular to the one direction.

With that feature, the number of the steering magnets used can be reduced and an installation space can be reduced, thus resulting in a smaller size of the irradiation facility.

(17) Further, to achieve the above object, the present invention provides a particle therapy system comprising an accelerator for accelerating a charged-particle beam to a set level of energy, a stationary irradiation facility for irradiating the charged-particle beam, and a beam transport unit for transporting the charged-particle beam extracted from the accelerator to the irradiation facility, wherein the particle therapy system further comprises a first beam position detecting unit arranged along an orbit of the charged-particle beam downstream of a most downstream one of magnets provided in the beam transport unit, and detecting a position at which the charged-particle beam passes; a second beam position detecting unit arranged along the orbit of the charged-particle beam downstream of the first beam position detecting unit, and detecting a position at which the charged-particle beam passes; a first steering magnet and a second steering magnet both provided in the beam transport unit upstream of the first beam position detecting unit; a first displacement amount computing unit for determining respective first displacement amounts, by which the position of the charged-particle beam is to be displaced by the first and second steering magnets, in accordance with detected signals outputted from the first and second beam position detecting units; and a first control unit for controlling respective excitation currents of the first and second steering magnets in accordance with the respective first displacement amounts.

(18) In above (17), preferably, the irradiation facility includes a first scatterer and a second scatterer arranged downstream of the first scatterer, and the first beam position detecting unit is arranged upstream of the second scatterer.

(19) In above (17), preferably, the irradiation facility includes a beam scanning unit for scanning the charged-particle beam, and the first beam position detecting unit is arranged upstream of the beam scanning unit.

DESCRIPTION OF THE PREFERRED EMBODIMENTS

Preferred embodiments of the present invention will be described below with reference to the drawings.

A first embodiment of the present invention will be described with reference to FIGS. 1 to 5.

Figure 1:
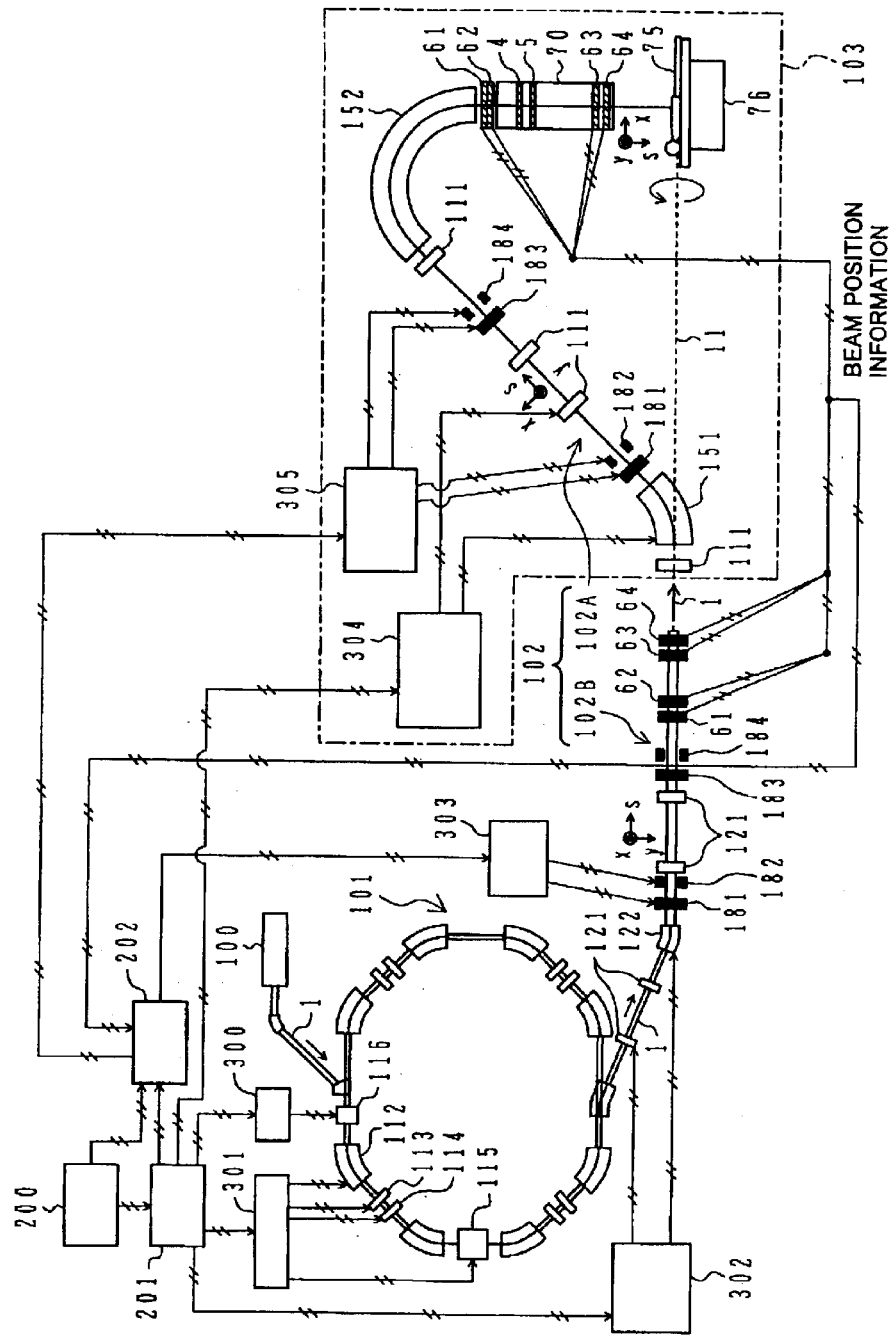
FIG. 1 is a system block diagram showing the overall construction of a particle therapy system according to a first embodiment of the present invention.

FIG. 1 is a system block diagram showing the overall construction of a particle therapy system according to a first embodiment of the present invention. For easier understanding of the overall construction, FIG. 1 includes, on the same drawing sheet, a side view showing the construction on the side of a rotating irradiation facility 103 (described later) and a plan view showing the construction of the remaining section on the side of a main accelerator 101 (described later). Correspondingly, to avoid misunderstanding, FIG. 1 also includes an x-coordinate axis representing a direction vertically upward from the drawing sheet, an s-coordinate axis representing a direction of beam propagation, and a y-coordinate in a direction perpendicular to both the x- and s-axes. Further, to avoid complication of the drawing, a flow of part of signals is not shown.

In FIG. 1, a particle therapy system of this embodiment comprises a pre-stage accelerator 100, a synchrotron type main accelerator 101, a beam transport system 102, a rotating irradiation facility 103, a main controller 200, an accelerator controller 201, and a steering magnet controller 202.

The main accelerator 101 comprises bending magnets 112 for bending a charged-particle beam orbiting in the main accelerator 101, an RF cavity 115 for applying energy to the orbiting charged-particle beam (e.g., a hydrogen ion beam or a carbon ion beam) and increasing the beam energy up to a desired setting value, quadrupole magnets 113 and multipole magnets 114 for applying magnetic fields to the orbiting charged-particle beam and bringing betatron oscillations into a resonance state, and an RF applying apparatus 116 for extraction, which applies RF to the orbiting charged-particle beam for increasing the betatron oscillations.

The bending magnets 112, the quadrupole magnets 113 and the multipole magnets 114 are excited under control with currents supplied from a power supply unit 301 for the accelerator, which is operated under control of the accelerator controller 201. The RF cavity 115 is supplied with electric power from the power supply unit 301 for the accelerator. Also, the RF applying apparatus 116 for extraction is supplied with electric power from an RF power supply unit 300 for extraction, which is operated under control of the accelerator controller 201.

The beam transport system 102 comprises a first beam transport system 102A positioned on the inlet side of the rotating irradiation facility 103, and a second beam transport system 102B positioned between the main accelerator 101 and the rotating irradiation facility 103.

The second beam transport system 102B comprises quadrupole magnets 121 for adjusting a beam size to transport a charged-particle beam 1 extracted from the accelerator 101 to the rotating irradiation facility 103, a bending magnet 122 for bending the orbit of the charged-particle beam 1, a pair of second x-direction beam position monitor 63 and second y-direction beam position monitor 64 for detecting the position (specifically the displacement and the gradient as described later) at which the charged-particle beam 1 passes (i.e., for confirming the beam orbit), a pair of first x-direction beam position monitor 61 and first y-direction beam position monitor 62 positioned upstream of the beam position monitors 63, 64, one pair of x-direction steering magnet 183 and y-direction steering magnet 184 disposed upstream of the beam position monitors 61, 62 for bending the beam 1 (i.e., applying correction bending amounts as described later) to correct the beam orbit, and another pair of x-direction steering magnet 181 and y-direction steering magnet 182 disposed upstream of the steering magnets 183, 184. Detected signals (beam position information) from the beam position monitors 61, 62, 63 and 64 in the second beam transport system 102B are inputted to the steering magnet controller 202.

The accelerator controller 201 controls a power supply unit 302 for the beam transport system magnets and adjusts excitation currents supplied to the quadrupole magnets 121, 111 and the bending magnets 122 through the power supply unit 302 for the beam transport system magnets, thereby controlling the amounts of excitations of these magnets.

Similarly to the second beam transport system 102B, the first beam transport system 102A comprises quadrupole magnets 111, a first bending magnet 151 and a second bending magnet 152 for bending the orbit of the charged-particle beam, one pair of x-direction (=direction of a bending plane of the bending magnets 151, 152) steering magnet 183 and y-direction (=direction perpendicular to the bending plane of the bending magnets 151, 152) steering magnet 184, and another pair of x-direction steering magnet 181 and y-direction steering magnet 182 disposed upstream of the steering magnets 183, 184.

The quadrupole magnets 111 and the bending magnets 151, 152 are excited and controlled with currents supplied from a power supply unit 304 for the irradiation facility, which is operated under control of the accelerator controller 201.

The rotating irradiation facility 103 includes the first beam transport system 102A communicating with the second beam transport system 102B, and an irradiation nozzle 70 upon which the charged-particle beam from the first beam transport system 102A is incident. The first beam transport system 102A and the irradiation nozzle 70 constitute an integral rotating unit (generally called a rotating gantry) that is rotatable about an axis 11 of rotation. Separately from the rotating irradiation facility 103, a non-rotating treatment bench (patient bed) 76, on which a patient 75 lies, is installed in a position locating on an extended line of the irradiation nozzle 70.

Downstream of a first scatterer 4 (scatterer disposed on the most upstream side), more practically, downstream of the irradiation nozzle 70 (or at a position within the irradiation nozzle 70 downstream of the first scatterer), one pair of x-direction beam position monitor 63 and y-direction beam position monitor 64 for detecting the position (specifically the beam displacement and the gradient as described later) at which the beam 1 passes (i.e., for confirming the beam orbit), as in the second beam transport system 102B. Also, another pair of x-direction beam position monitor 61 and y-direction beam position monitor 62 are disposed upstream of the beam position monitors 63, 64 and upstream of a second scatterer 5 disposed in the irradiation nozzle 70, more practically, upstream of the irradiation nozzle 70 (or at a position within the irradiation nozzle 70 upstream of the second scatterer 5). Those beam position monitors 61, 62, 63 and 64 are positioned downstream of all magnetic force elements (magnets) arranged in the particle therapy system of this embodiment, including the above-mentioned ones, in the direction of beam propagation, and no magnetic force elements are disposed between the beam position monitors 61, 62 and the beam position monitors 63, 64. Additionally, the second scatterer 5 is disposed downstream of the first scatterer 4 within the irradiation nozzle 70. Detected signals (beam position information) from the beam position monitors 61, 62, 63 and 64 in the rotating irradiation facility 103 are inputted to the steering magnet controller 202.

The accelerator controller 201 and the steering magnet controller 202 are controlled by the main controller 200 in accordance with various patient data. The patient data has been collected beforehand in relation to a treatment program and includes, e.g., the energy of the charged-particle beam required for the treatment and the rotational angle of the rotating irradiation facility.

The accelerator controller 201 has, as described above, the functions of controlling extraction of the beam from the pre-stage accelerator 100 to the main accelerator 101, acceleration of the charged-particle beam orbiting in the main accelerator 101 to increase the beam energy to a level required for the treatment, extraction of the accelerated beam into the second beam transport system 102B, and transport of the charged-particle beam in the first beam transport system 102A and the rotating irradiation facility 103 through the RF power supply unit 300 for extraction, the power supply unit 301 for the accelerator, the power supply unit 302 for the beam transport system magnets, and the power supply unit 304 for the irradiation facility.

The steering magnet controller 202 determines respective excitation amounts of the steering magnets 181, 182, 183 and 184 to obtain the kick amounts (described later in more detail) required for correcting the beam position (position of the charged-particle beam) so as to lie on the predetermined orbit (i.e., the design orbit of the irradiation nozzle 70 in this embodiment) in accordance with the position information of the charged-particle beam (beam position information) from the beam position monitors 61, 62, 63 and 64 in the second beam transport system 102B and the rotating irradiation facility 103. Then, based on the determined extraction amounts, the steering magnet controller 202 controls a power supply unit 303 for the beam transport system steering magnets and a power supply unit 305 for the irradiation facility steering magnets, thereby controlling excitation currents supplied from the power supply unit 303 for the beam transport system steering magnets to the steering magnets 181, 182, 183 and 184 in the second beam transport system 102B and controlling excitation currents supplied from the power supply unit 305 for the irradiation facility steering magnets to the steering magnets 181, 182, 183 and 184 in the first beam transport system 102A. As a result, the respective excitation amounts of the steering magnets in the first beam transport system 102A and the second beam transport system 102B are controlled. In this connection, the relationships between current values supplied to the steering magnets 181 to 184 and the kick amounts, by which the charged-particle beam 1 is kicked by respective magnetic field generated corresponding to the current values, are determined in advance.

In the particle therapy system of this embodiment having the construction described above, the charged-particle beam 1 of low energy enters the main accelerator 101 from the pre-stage accelerator 100, and is accelerated by the main accelerator 101 so as to have energy required for the treatment. Thereafter, the accelerated charged-particle beam 1 is transported to a treatment room (not shown) from the second beam transport system 102B, then introduced to the irradiation nozzle 70 through the first beam transport system 102A in the rotating irradiation facility 103, and then irradiated to the diseased area after being shaped by the irradiation nozzle 70.

In the particle therapy system having the basic construction and operating as described above, the features of this embodiment reside in determining the correction bending amounts of the steering magnets 181 to 184 based on approximation models using transfer matrices, exciting and controlling the steering magnets 181 to 184, and correcting the orbit of the charged-particle beam 1 to be finally coincident with the design orbit of the irradiation nozzle 70. Those features will be described in more detail in sequence.

(1) Definition of Approximation Models

The position and gradient of the beam orbit in the beam transport system can be calculated using transfer matrices that represent the bending magnets, the quadrupole magnets, the steering magnets, and drift spaces (free spaces which include no magnets or the likes and do not affect the beam orbit) between the magnets.

As a result of studies conducted by the inventors, it has been found that, when tilt angles of the bending magnets and alignment errors of the quadrupole magnets are small, the change amounts of the position and gradient of the beam orbit caused by the bending magnets and the quadrupole magnets can be approximated by a method of separating those change amounts from respective transfer matrices and adding the change amounts of the position and gradient after the beam has passed the equipment. This point is described below.

<1> Approximation of Transfer Matrices of Bending Magnets

First, for the bending magnets, when each magnet has an alignment tilt angle (=angle of a rotational alignment error with the direction of beam propagation being defined as the axis of rotation, an ideal value is 0 degree), the transfer matrices can be approximated by the following formulae (1-1) and (1-2) for the horizontal direction and the vertical direction, respectively. In those formulae, $\rho$ is the bending radius, $\theta$ is the bending angle, and $\Phi$ is the tilt angle.

Horizontal Direction:

$$\begin{pmatrix} x \\ x' \end{pmatrix} = \begin{pmatrix} \cos\theta & \rho\sin\theta \\ -\frac{\sin\theta}{\rho} & \cos\theta \end{pmatrix} \begin{pmatrix} x_0 \\ x'_0 \end{pmatrix} \quad (1\text{-}1)$$

Vertical Direction:

$$\begin{pmatrix} y \\ y' \end{pmatrix} = \begin{pmatrix} 1 & \rho\theta \\ 0 & 1 \end{pmatrix} \begin{pmatrix} y_0 \\ y'_0 \end{pmatrix} + \begin{pmatrix} \frac{\rho\sin\phi \times \theta^2}{2} \\ \sin\phi \times \theta \end{pmatrix} \quad (1\text{-}2)$$

In those formulae (1-1) and (1-2), the first term represents an ideal orbit when the tilt angle is zero, and the second term represents an effect of the tilt angle. Note that, for the horizontal direction, the second term is omitted because it is expressed by a term of second degree of the tilt angle $\Phi$ having a very small value and hence so small as negligible.

<2> Approximation of Transfer Matrices of Quadrupole Magnets

Next, for the quadrupole magnets, when each magnet has an alignment error in a plane perpendicular to the direction of beam propagation, the transfer matrices (horizontal direction) can be expressed by the following formulae (1-3) and (1-4). In those formulae, K is the absolute value of a value obtained by dividing a field gradient by a magnetic rigidity B$\rho$, L is the magnetic length, and $\zeta$ is the amount of alignment error.

Focusing Type:

$$\begin{pmatrix} x \\ x' \end{pmatrix} = \begin{pmatrix} \cos(\sqrt{K}L) & \frac{1}{\sqrt{K}}\sin(\sqrt{K}L) \\ -\sqrt{K}\sin(\sqrt{K}L) & \cos(\sqrt{K}L) \end{pmatrix} \begin{pmatrix} x_0 \\ x'_0 \end{pmatrix} + \begin{pmatrix} \{1-\cos(\sqrt{K}L)\}\zeta \\ \{\sqrt{K}\sin(\sqrt{K}L)\}\zeta \end{pmatrix} \quad (1\text{-}3)$$

Defocusing Type:

$$\begin{pmatrix} x \\ x' \end{pmatrix} = \begin{pmatrix} \cosh(\sqrt{K}L) & \frac{1}{\sqrt{K}}\sinh(\sqrt{K}L) \\ \sqrt{K}\sinh(\sqrt{K}L) & \cosh(\sqrt{K}L) \end{pmatrix} \begin{pmatrix} x_0 \\ x'_0 \end{pmatrix} + \begin{pmatrix} \{1-\cosh(\sqrt{K}L)\}\zeta \\ \{-\sqrt{K}\sinh(\sqrt{K}L)\}\zeta \end{pmatrix} \quad (1\text{-}4)$$

In those formulae (1-3) and (1-4), the first term represents an ideal orbit when the alignment error is zero, and the second term represents an effect of the alignment error. Note that the transfer matrices for the vertical direction are expressed by replacing factors of focusing and defocusing actions in the above transfer matrices with each other.

<3> Evaluation of Correction Amount by Steering Magnet

When correcting the beam orbit in the beam transport system, it is possible to apply a correction kick for changing the beam gradient by the steering magnet, and to confirm the effect of the applied kick as a change of the beam position using a beam position monitor installed downstream of the steering magnet. In this connection, it has been found from studies conducted by the inventors that, by employing the approximation, models described in above <1> and <2>, in evaluation of the gradient correction amount applied by the steering magnetin evaluation of the gradient correction amount applied by the steering magnet, the correction can be regarded as a single kick and hence as an application of only a gradient change (kick amount) from the steering magnet. This point is described below in more detail with reference to FIG. 2. Note that the effect of alignment errors in the direction of beam propagation is so small and therefore is neglected here.

Figure 2:
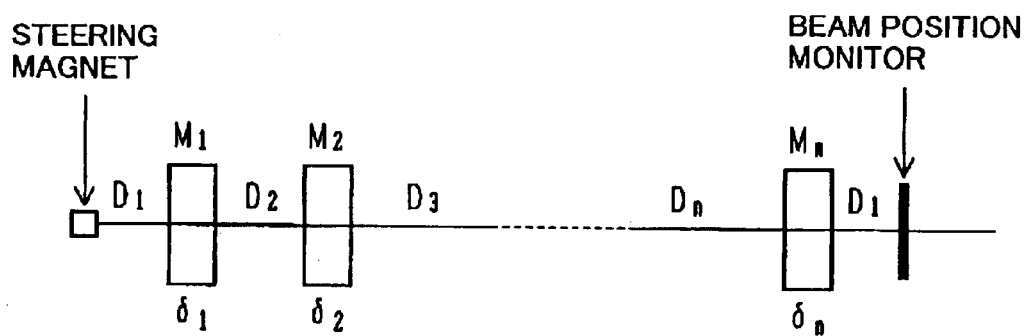
FIG. 2 is a schematic view of a beam transport system when the system includes alignment errors.

FIG. 2 is a schematic view of the beam transport system when the system includes alignment errors. In FIG. 2, $D_i$ is a transfer matrix representing an i-th drift space, and $M_i$ is a transfer matrix representing an i-th magnet. Also, $\vec{\delta_i}$ (in the following description of this specification, "→" affixed at an upper right corner of a preceding character is a symbol substituted for an arrow indicative of a vector or a bold font indicative of a matrix) is a vector representing a change of the displacement/gradient caused by the alignment error of an i-th piece of equipment. Further, $\vec{x_i}$ is a vector representing the displacement/gradient after passing the i-th piece of equipment, and $\vec{x_0}$ is a vector representing the displacement/gradient at the steering magnet. $A_i = M_i D_i$ is held. In addition, $\vec{k}$ is a vector representing a kick applied by the steering magnet and is expressed by:

$$k = \begin{pmatrix} 0 \\ k \end{pmatrix} \quad (1\text{-}5)$$

In FIG. 2, values of the displacement/gradient at the beam position monitor before correction are expressed by:

$$\vec{x_1} = A_1 \vec{x_0} + \vec{\delta_1} \quad (1\text{-}6)$$

$$\vec{x_2} = A_2 \vec{x_1} + \vec{\delta_2}$$

$$= A_2(A_1 \vec{x_0} + \vec{\delta_1}) + \vec{\delta_2}$$

$$= A_2 A_1 \vec{x_0} + A_2 \vec{\delta_1} + \vec{\delta_2}$$

...

...

...

$$\vec{x_n} = A_n \vec{x_{n-1}} + \vec{\delta_n}$$

$$= (A_n A_{n-1} \cdots A_3 A_2 A_1)\vec{x_0} + (A_n A_{n-1} \cdots A_3 A_2)\vec{\delta_1} +$$

$$(A_n A_{n-1} \cdots A_3)\vec{\delta_2} + \ldots + A_n \vec{\delta_{n-1}} + \vec{\delta_n}$$

$$\vec{x_f} = D_f \vec{x_n}$$

$$= (D_f A_n A_{n-1} \cdots A_3 A_2 A_1)\vec{x_0} + (D_f A_n A_{n-1} \cdots A_3 A_2)\vec{\delta_1} +$$

$$(D_f A_n A_{n-1} \cdots A_3)\vec{\delta_2} + \ldots + D_f A_n \vec{\delta_{n-1}} + D_f \vec{\delta_n}$$

Next, when the correction kick $\vec{k}$ is newly applied with the steering function of the steering magnet, an orbit vector at a steering magnet outlet is expressed by:

$$\vec{x_0} \rightarrow \vec{x_0} + \vec{k}$$

Accordingly, the beam orbit after the correction is expressed as given below using an affix c:

$$\vec{x_{1c}} = A_1(\vec{x_0} + \vec{k}) + \vec{\delta_1} \quad (1\text{-}7)$$

$$\vec{x_{2c}} = A_2 \vec{x_{1c}} + \vec{\delta_2}$$

$$= A_2\{A_1(\vec{x_0} + \vec{k}) + \vec{\delta_1}\} + \vec{\delta_2}$$

$$= A_2 A_1 \vec{x_0} + A_2 A_1 \vec{k} + A_2 \vec{\delta_1} + \vec{\delta_2}$$

...

...

...

$$\vec{x_{nc}} = A_n \vec{x_{n-1,c}} + \vec{\delta_n}$$

$$= (A_n A_{n-1} \cdots A_3 A_2 A_1)\vec{x_0} + (A_n A_{n-1} \cdots A_3 A_2 A_1)\vec{k} +$$

$$(A_n A_{n-1} \cdots A_3 A_2)\vec{\delta_1} + (A_n A_{n-1} \cdots A_3)\vec{\delta_2} + \ldots + A_n \vec{\delta_{n-1}} + \vec{\delta_n}$$

$$\vec{x_{fc}} = D_f \vec{x_{nc}}$$

$$= (D_f A_n A_{n-1} \cdots A_3 A_2 A_1)\vec{x_0} + (D_f A_n A_{n-1} \cdots A_3 A_2 A_1)\vec{k} +$$

$$(D_f A_n A_{n-1} \cdots A_3 A_2)\vec{\delta_1} + (D_f A_n A_{n-1} \cdots A_3)\vec{\delta_2} + \ldots +$$

$$D_f A_n \vec{\delta_{n-1}} + D_f \vec{\delta_n}$$

From comparison between the above formulae (1-6) and (1-7), $\vec{x_{fc}}$ is expressed as given below using the value $\vec{X_f}$ before the correction:

$$\vec{x_{fc}} = (D_f A_n A_{n-1} \cdots A_3 A_2 A_1)\vec{k} + \vec{x_f} \quad (1\text{-}8)$$

It is thus understood that, as represented by the above formula (1-8), the effect of a kick applied with the steering function of the steering magnet is represented in the form in which the term of $(D_f A_n A_{n-1} \ldots A_3 A_2 A_1)\vec{k}$ is added to the term $\vec{x_f}$ including the effect of alignment errors before the correction, by employing the approximation models described in above <1> and <2>. In other words, it has been confirmed that an orbit change caused with the steering kick can be evaluated by multiplying an ideal transition matrix $(=D_f A_n A_{n-1} \ldots A_3 A_2 A_1$ in the above example), which is free from the effect of alignment errors, by the correction kick vector $(=\vec{k}$ in the above example).

(2) Principles of Orbit Correction in this Embodiment Using Approximation Models Described above A description is now made of the case in which the approximation models described in above (1) are practically applied to the orbit correction in the particle therapy system of this embodiment.

Generally, of optical equipment arranged in a beam transport system, transfer matrices $M_{BMx}$, $M_{BMy}$, $M_{QF}$ and $M_{QD}$ of a bending magnet (BM), a focusing quadrupole magnet (QF), and a defocusing quadrupole magnet (QD) can be expressed by the following formulae (2-1), (2-2), (2-3) and (2-4), respectively. In these formulae, $\rho$ and $\theta$ represent the bending radius [m] and the bending angle [rad] of the bending magnet, respectively, and K and L represents the K value [1/m$^2$] and the magnetic length [m] of the quadrupole magnet.

$$M_{BMx} = \begin{pmatrix} \cos\theta & \rho\sin\theta \\ -\dfrac{\sin\theta}{\rho} & \cos\theta \end{pmatrix} \quad (2\text{-}1)$$

$$M_{BMy} = \begin{pmatrix} 1 & \rho\theta \\ 0 & 1 \end{pmatrix} \quad (2\text{-}2)$$

-continued $$M_{QF} = \begin{pmatrix} \cos\sqrt{K}L & \frac{1}{\sqrt{K}}\sin\sqrt{K}L \\ -\sqrt{K}\sin\sqrt{K}L & \cos\sqrt{K}L \end{pmatrix} \quad (2\text{-}3)$$

$$M_{QD} = \begin{pmatrix} \cosh\sqrt{K}L & \frac{1}{\sqrt{K}}\sinh\sqrt{K}L \\ \sqrt{K}\sinh\sqrt{K}L & \cosh\sqrt{K}L \end{pmatrix} \quad (2\text{-}4)$$

Here, though depending on the method used for forming the irradiation field, the position accuracy required for the beam 1 introduced to the irradiation nozzle 70 is usually on the submillimeter order and the accuracy required for the orbit gradient is not more than about 1 mrad. Since the irradiation nozzle 70 is designed on the basis of the design orbit of the charged-particle beam 1 as described above, both the orbit displacement and gradient of the charged-particle beam 1 must be ideally zero. Also, in the so-called rotating irradiation facility like 103 in this embodiment, at the time when the charged-particle beam 1 enters the rotating irradiation facility 103, both the orbit displacement and gradient of the charged-particle beam 1 are desirably zero so that the axis of the incident beam coincides with the axis 11 of rotation of the rotating gantry.

In order to set those two parameters, i.e., the displacement and the gradient, to particular values, this embodiment employs two pairs of steering magnets 181, 182, 183 and 184 in each of the first beam transport system 102A and the second beam transport system 102B.

Figure 3:
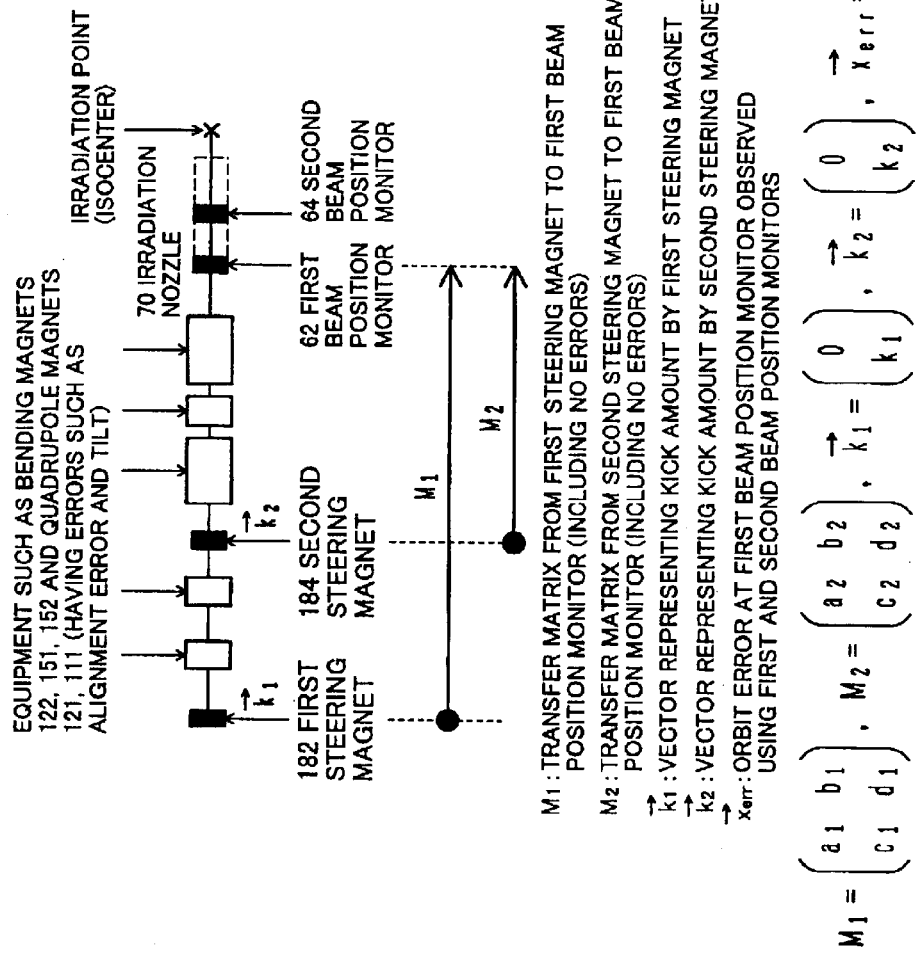
FIG. 3 is a schematic view of a beam transport system provided with two steering magnets and two beam position monitors within an irradiation nozzle.

FIG. 3 is a schematic view of a beam transport system provided with two steering magnets and two beam position monitors within an irradiation nozzle on assumption of each of the first beam transport system 102A and the second beam transport system 102B in this embodiment. With reference to FIG. 3, a description is now made in detail of the principles for determining the kick amounts of two steering magnets, which are required for correcting both the beam displacement and gradient at the irradiation nozzle 70 to zero, based on the review discussed above. While the description is made of, by way of example, correction in the x-direction, it is a matter of course that correction in the y-direction can also be performed using similar equipment and manner.

By utilizing the approximation models in above <1> and <2>, as reviewed in above (1)<3>, the effect of the orbit correction performed by the two steering magnets in FIG. 3 can be determined just by multiplying the kick amount applied from each of the steering magnets by an ideal transition matrix, which is free from alignment errors.

More specifically, assuming that the first and second steering magnets 182, 184 apply kick amounts $k_1^{\rightarrow}$ and $k_2^{\rightarrow}$, respectively, orbit changes $x_1^{\rightarrow}$ and $x_2^{\rightarrow}$ caused upon the application of the kick amounts at the first beam position monitor 62 can be expressed as given below using transfer matrices:

$$\vec{x}_1 = M_1 \vec{k}_1 \quad (2\text{-}5)$$

$$\vec{x}_2 = M_2 \vec{k}_2 \quad (2\text{-}6)$$

To modify an orbit error $x_{err}^{\rightarrow}$ observed at the first beam position monitor 62 and to make zero both the beam displacement and gradient, the following formula must be satisfied:

$$\vec{x}_1 + \vec{x}_2 + \vec{x}_{err} = \vec{0} \quad (2\text{-}7)$$

Stated otherwise, the kick amounts $k_1^{\rightarrow}$ and $k_2^{\rightarrow}$ meeting the following formula require to be determined:

$$\begin{pmatrix} a_1 & b_1 \\ c_1 & d_1 \end{pmatrix}\begin{pmatrix} 0 \\ k_1 \end{pmatrix} + \begin{pmatrix} a_2 & b_2 \\ c_2 & d_2 \end{pmatrix}\begin{pmatrix} 0 \\ k_2 \end{pmatrix} + \begin{pmatrix} x_{err} \\ x'_{err} \end{pmatrix} = \quad (2\text{-}8)$$

$$\begin{pmatrix} b_1 & b_2 \\ d_1 & d_2 \end{pmatrix}\begin{pmatrix} k_1 \\ k_2 \end{pmatrix} + \begin{pmatrix} x_{err} \\ x'_{err} \end{pmatrix} = \begin{pmatrix} 0 \\ 0 \end{pmatrix}$$

Accordingly, on assumption of;

$$M_{cor} = \begin{pmatrix} b_1 & b_2 \\ d_1 & d_2 \end{pmatrix} \quad (2\text{-}9)$$

the kick amounts $k_1^{\rightarrow}$ and $k_2^{\rightarrow}$ can be determined as given below using an inverse matrix of above $M_{cor}$:

$$\begin{pmatrix} k_1 \\ k_2 \end{pmatrix} = -M_{cor}^{-1}\begin{pmatrix} x_{err} \\ x'_{err} \end{pmatrix} \quad (2\text{-}10)$$

At this time, the orbit error $x_{err}^{\rightarrow}$ can be determined as given below using respective position information $X_1^{\rightarrow}$, $X_2^{\rightarrow}$ detected by the two beam position monitors 62, 64 and distance L between them:

$$\vec{x}_{err} = (x_{err}, x'_{err}) = \left(X_1, \frac{X_2 - X_1}{L}\right) \quad (2\text{-}11)$$

Also, although $M_{cor}$ to be determined from the transfer matrix can be determined from an ideal transfer matrix as described above, it may be determined from the relationships between the kick amounts $k_1^{\rightarrow}$, $k_2^{\rightarrow}$ and the position information $X_1^{\rightarrow}$, $X_2^{\rightarrow}$ so as to reflect the actual system when an adjustment is actually carried out using the beam 1.

Thus, according to the above-described method, the displacement and the gradient at the first beam position monitor 62 and an ideal transfer matrix of each piece of equipment arranged downstream of the steering magnet 182 or 184 are only required, whereas the alignment error and the tilt amount of each piece of equipment and values of the displacement and the gradient of the beam 1 transported to the position of the first steering magnet 182 are not required for the purpose of calculations (in other words, the beam orbit can be corrected even when it is unknown at all how large the alignment error is in fact or what displacement and gradient are caused in each transport element caused by such an alignment error). Conditions required by the above-described method of calculating the correction amounts are as follows: (a) two beam position monitors are installed in a state in which there are no beam optical equipment (i.e., bending magnets and quadrupole magnets) between them, and (b) two steering magnets are installed upstream of those two beam position monitors. In this embodiment, as seen from the above description, the first beam transport system 102A and the second beam transport system 102B are constructed so as to satisfy those conditions.

In practice, contributions of multiple-pole (primarily hexapole) components of the bending magnets and multiple-pole (octupole) components of the quadrupole magnets are estimated. It is however thought that those contributions are small because those magnets are usually designed and manufactured on condition that the multiple-pole components are sufficiently reduced.

(3) Orbit Adjusting Sequence in this Embodiment

A description is now made of an actual sequence for adjusting the orbit of the charged-particle beam in the particle therapy system of this embodiment based on the principles of above (2). The orbit adjustment is performed as a part of a series of operations for adjusting the charged-particle beam prior to the treatment, i.e., before the patient, to whom the charged-particle beam is irradiated, lies in the position on the extended line of the irradiation nozzle 70. The orbit adjustment is performed under linked control of the main controller 200, the accelerator controller 201, a gantry rotation controller (not shown), and the steering magnet controller 202. A sequence of steps for orbit correction control performed by the steering magnet controller 202 will be described below with reference to FIG. 4.

Figure 4:
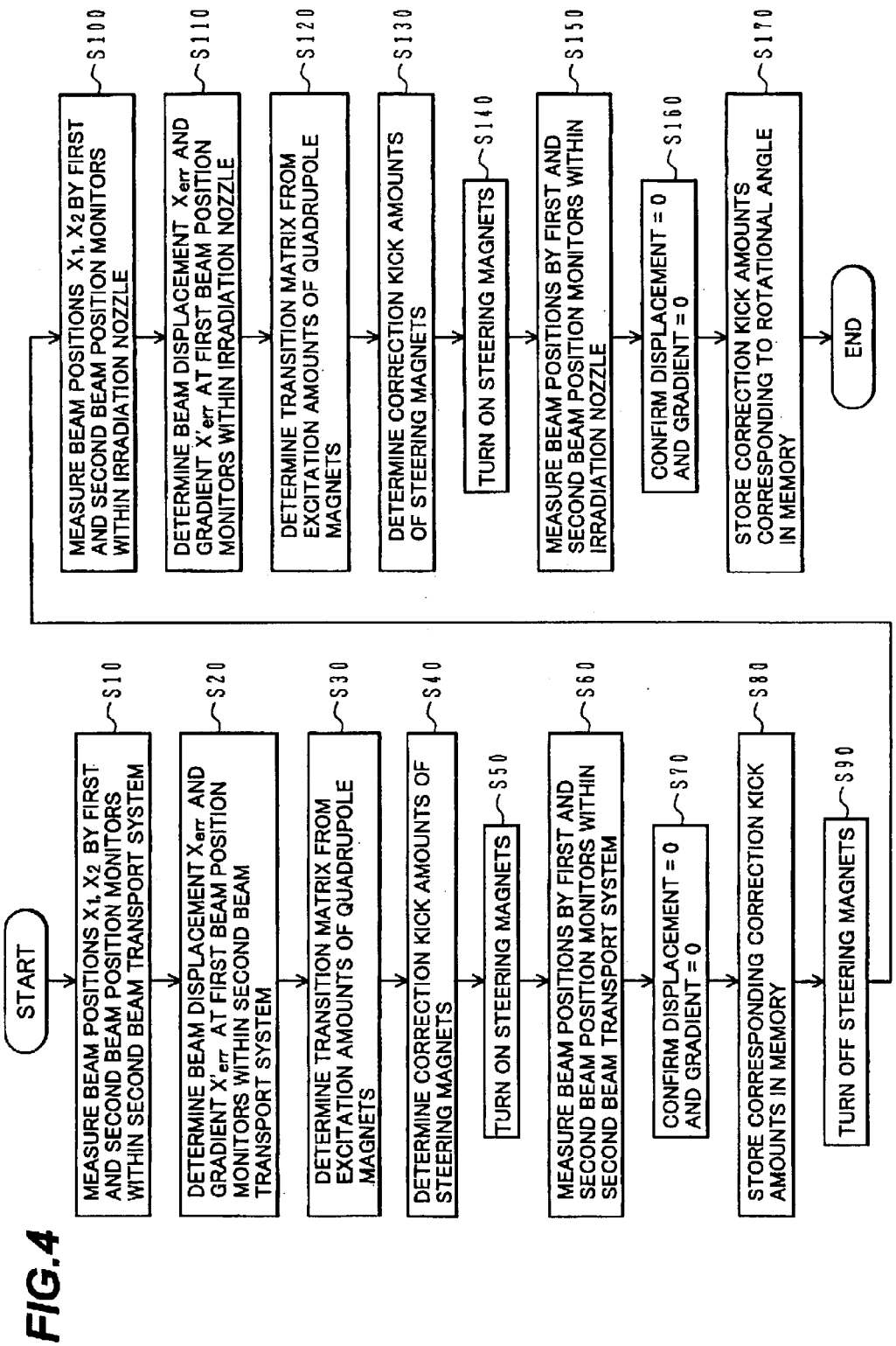
FIG. 4 is a flowchart showing beam correction control steps performed by an accelerator controller and a steering magnet controller, which are provided in the particle therapy system according to the first embodiment of the present invention.

A flow shown in FIG. 4 comprises two sequences of steps 10 to 80 for correcting the beam orbit in the second beam transport system 102B (i.e., making correction so that the beam axis coincides with the axis 11 of rotation), and steps 90 to 170 for correcting the beam orbit in the first beam transport system 102A (or on the rotating gantry side) (i.e., making correction so that the beam axis finally coincides with the design orbit of the irradiation nozzle 70).

First, the main controller 200 outputs a start-up signal to the accelerator controller 201 and the steering magnet controller 202 beforehand. Upon receiving the start-up signal, the accelerator controller 201 controls the RF power supply unit 300 for extraction of the charged-particle beam, the power supply unit 301 for the accelerator, and the power supply unit 302 for the beam transport system magnets. Also, upon receiving the start-up signal, the steering magnet controller 202 controls the power supply unit 303 for the beam transport system steering magnets, causing the beam to pass through the second beam transport system 102B. Then, the steering magnet controller 202 performs correction of the beam orbit in the second beam transport system 102B through steps 10 to 80.

More specifically, in step 10, the steering magnet controller 202 receives beam position detected signals from the first and second beam position monitors 61, 62, 63 and 64 disposed in the second beam transport system 102B.

Thereafter, in step 20, the steering magnet controller 202 computes the displacement and the gradient of the charged-particle beam at the first beam position monitors 61, 62 from the above formula (2-11) in accordance with the detected signals received in above step 10.

Subsequently, in step 30, an ideal transfer matrix (transition matrix) between the first steering magnets 181, 182 and the first beam position monitors 61, 62 is computed from respective excitation amounts of the quadrupole magnets 121, 121 positioned between the first steering magnets 181, 182 and the first beam position monitors 61, 62. An ideal transfer matrix (transition matrix) between the second steering magnets 183, 184 and the first beam position monitors 61, 62 is also computed.

Then, in step 40, first kick amounts of the first and second steering magnets 182, 184 are computed from the above formulae (2-9) and (2-10) by using the beam displacement and gradient computed in above step 20 and the transition matrix computed in above step 30. Thereafter, in step 50, the power supply unit 303 for the beam transport system steering magnets is controlled to adjust excitation currents supplied to the first and second steering magnets 182, 184 so that the computed first kick amounts are obtained.

Subsequently, in step 60, the first and second beam position monitors 61, 62, 63 and 64 detect the beam position in the excited state of the steering magnets. If the displacement=0 and the gradient=0 are confirmed in step 70, the first kick amounts (first correction kick amounts) at that time are stored in a storage means (not shown), e.g., a memory in the steering magnet controller 202, in step 80.

After the completion of step 80, the steering magnet controller 202 performs correction of the beam orbit in the first beam transport system 102A through steps 90 to 170. First, as a preparatory procedure, excitations of all the steering magnets 181, 182, 183 and 184 are stopped via the power supply unit 303 for the beam transport system steering magnets and the power supply unit 305 for the irradiation facility steering magnets.

When the excitation stopping control comes to an end, the steering magnet controller 202 outputs a temporary standby signal to the main controller 200. Upon receiving the temporary standby signal, the main controller 200 inputs a gantry rotational angle, which corresponds to the treatment plan (irradiation plan), to the gantry rotation controller (not shown). In accordance with the inputted rotational angle, the gantry rotation controller drives a rotation driver (not shown) for rotating the rotating unit (gantry) to a predetermined angle. Upon the completion of the rotation, an end-of-rotation signal is outputted to the main controller 200. Then, the steering magnet controller 202 receives a steering-magnet ON signal from the main controller 200 and excites all the steering magnets in the first beam transport system 102A and the second beam transport system 102B, whereupon the charged-particle beam extracted from the main accelerator 101 is introduced to pass through the first beam transport system 102A and the second beam transport system 102B.

Thereafter, in step 100, the steering magnet controller 202 receives beam position detected signals from the first and second beam position monitors 61, 62, 63 and 64 disposed in the irradiation nozzle 70.

Then, in step 110, the steering magnet controller 202 computes the beam displacement and gradient at the first beam position monitors 61, 62 from the above formula (2-11) in accordance with the detected signals received in above step 100.

Subsequently, in step 120, an ideal transfer matrix (transition matrix) between the first steering magnets 181, 182 and the first beam position monitors 61, 62 is computed from respective excitation amounts of the quadrupole magnets 111, 111, 111 and the bending magnet 152 all positioned between the first steering magnets 181, 182 and the first beam position monitors 61, 62. An ideal transfer matrix (transition matrix) between the second steering magnets 183, 184 and the first beam position monitors 61, 62 is also computed from respective excitation amounts of the quadrupole magnet 111 and the bending magnet 152 both positioned therebetween.

Then, in step 130, second kick amounts of the first and second steering magnets 182, 184 are computed from the above formulae (2-9) and (2-10) by using the beam displacement and gradient computed in above step 110 and the transition matrix computed in above step 120. Thereafter, in step 140, the power supply unit 303 for the beam transport system steering magnets is controlled to adjust excitation currents supplied to the first and second steering magnets 182, 184 so that the computed second kick amounts are obtained.

Subsequently, in step 150, the first and second beam position monitors 61, 62, 63 and 64 detect the beam position in the excited state of the steering magnets. If the displacement=0 and the gradient=0 are confirmed in step 160, the second kick amounts (second correction kick amounts) at that time are stored in the storage means in step 170. After execution of the processing of step 170, the accelerator controller 201 stops the extraction of the charged-particle beam from the main accelerator 101 upon receiving a command from the main controller 200.

As understood from the above description, the steering magnet controller 202 essentially includes first displacement amount computing appratus for computing first displacement amounts (second kick amounts) by which the charged-particle beam is displaced by the steering magnets in the irradiation facility 103, first cotrol system for controlling excitation currents supplied to the steering magnets in the irradiation facility 103 in accordance with the first displacement amounts, second displacement amount computing appratus for computing second displacement amounts (first kick amounts) by which the charged-particle beam is displaced by the steering magnets in the second beam transport system 102B, and second control system for controlling excitation currents supplied to the steering magnets in the second beam transport system 102B in accordance with the second displacement amounts. The first displacement amount computing appratus executes the processing of above steps 100 to 130 and steps 150 to 170, and the first cotrol system executes the control in step 140. The second displacement amount computing appratus executes the processing of above steps 20 to 40 and steps 60 to 80, and the second control system executes the control in step 50.

After adjusting the orbit of the charged-particle beam as described above, the treatment bench 76 is moved to align the diseased area of the patient lying on the treatment bench 76 with the irradiation nozzle 70. Then, the main controller 200 outputs a treatment start signal to the various controllers in accordance with an instruction inputted by an operator. Under the actions of the various controllers such as the accelerator controller 201, the charged-particle beam is extracted from the main accelerator 101 and irradiated to the patient through the irradiation nozzle 70. At this time, the steering magnet controller 202 controls respective excitation currents supplied to the steering magnets provided in the second beam transport system 102B in accordance with the first kick amounts stored in the storage means and also controls respective excitation currents supplied to the steering magnets provided in the first beam transport system 102A in accordance with the second kick amounts stored in the storage means instead of using respective output signals from the beam position monitors. With that control, the displacement and the gradient of the charged-particle beam irradiated to the patient through the irradiation nozzle 70 can be each made zero (0).

(4) Operation and Advantages of this Embodiment

The operation of the method of correcting the beam orbit in the above-described particle therapy system of this embodiment will be described with reference to a comparable example.

Figure 5:
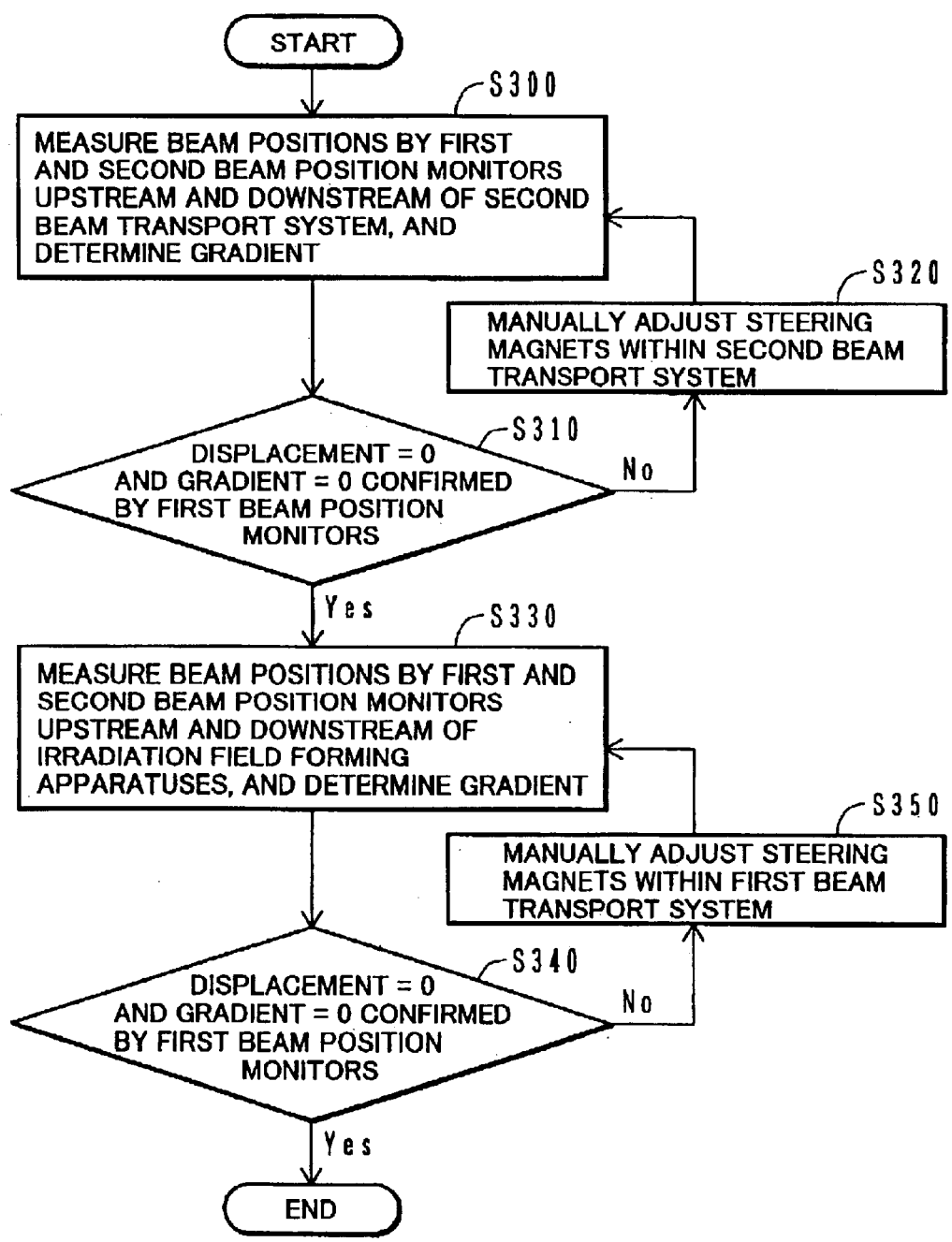
FIG. 5 is a flowchart showing primary steps of a beam orbit correcting method in a comparative example almost corresponding to the prior art.

FIG. 5 is a flowchart showing primary steps of a beam orbit correcting method in a comparative example almost corresponding to the prior art described above. For easier comparison, in the following description, components corresponding to those in the particle therapy system of this embodiment are denoted by the same reference symbols.

In FIG. 5, in first step 300, beam position detected signals are received which are obtained from the first and second beam position monitors 61, 62, 63 and 64 disposed in the second beam transport system 102B on the relatively upstream and downstream sides, and the beam gradients are computed from the detected signals.

Then, in step 310, the beam position and gradient at the first beam position monitors 61, 62 are displayed on an appropriate display, and the operator determines whether the displacement and the gradient of the beam position are each zero (0). If any of the beam displacement and gradient is not zero (0), excitation amounts of the first and second steering magnets 181, 182, 183 and 184 disposed in the second beam transport system 102B are manually adjusted in step 320. Thereafter, the control flow returns to step 300 to repeat the same processing steps as those described above. In such a way, the operator repeats the manual adjustment on a trial-and-error basis until the beam displacement and gradient each become zero (0) in step 310.

If the displacement and the gradient of the beam position at the first beam position monitors 61, 62 are each zero (0), a decision condition in step 310 is satisfied and the control flow proceeds to step 330.

In step 330, as in above step 300, beam position detected signals are received which are obtained from the first and second beam position monitors 61, 62, 63 and 64 disposed in the irradiation nozzle 70 on the relatively upstream and downstream sides, and the beam gradients are computed from the detected signals.

Then, in step 340, as in above step 310, the beam position and gradient at the first beam position monitors 61, 62 are displayed on an appropriate display, and the operator determines whether the displacement and the gradient of the beam position are each zero (0). If any of the beam displacement and gradient is not zero (0), excitation amounts of the first and second steering magnets 181, 182, 183 and 184 disposed in the first beam transport system 102A are manually adjusted in step 350. Thereafter, the control flow returns to step 330 to repeat the same processing steps as those described above. In such a way, the operator repeats the manual adjustment on a trial-and-error basis until the beam displacement and gradient each become zero (0) in step 340.

If the displacement and the gradient of the beam position at the first beam position monitors 61, 62 are each zero (0), a decision condition in step 340 is satisfied and the operation of correcting the beam orbit is all completed, whereby the control flow is brought into an end.

Thus, in the comparative example described above, the operator carries out the manual adjustment on a trial-and-error basis by manually increasing or decreasing the excitation amounts (kick amounts) of the steering magnets, while looking at a tendency of resulting changes in the beam displacement and gradient, so that the position of the charged-particle beam 1 coincides with the design orbit. Accordingly, a lot of labor and time have been required for the operation of correcting the beam orbit.

Particularly, in the rotating irradiation facility 103, as employed in the particle therapy system of this embodiment shown in FIG. 1, wherein the rotating irradiator (rotating gantry) is rotatably installed about the axis 11 of rotation so that the beam can be irradiated from a proper angular position in match with the position and condition of the diseased area, the amounts of flexures, deformations, etc. of various components caused by their own weights change depending on the rotational angle of the rotating gantry, and the alignment errors also change depending on the rotational angle. Hence, the operation of correcting the beam orbit must be repeated on a trial-and-error basis whenever the rotational angle of the rotating gantry (rotating irradiation facility 103) is changed, thus resulting in a very troublesome operation.

In contrast, with the method of correcting the beam orbit in the particle therapy system according to this embodiment, as described in above (1) to (3), the correction kick amounts of the first and second steering magnets 181, 182, 183 and 184 based on the approximation models using respective transfer matrices of the various transport elements are determined in accordance with the detected signals from the first and second beam position monitors 61, 62, 63 and 64, and the steering magnet controller 202 controls respective excitation currents supplied to the first and second steering magnets 181, 182, 183 and 184 via the power supply unit 303 for the beam transport system steering magnets and the power supply unit 305 for the irradiation facility steering magnets so that the determined correction kick amounts are given to the beam 1. Thus, the beam 1 can be corrected to be coincident with the predetermined design orbit. Accordingly, labor and time required for the orbit correction can be greatly reduced and the correcting operation can be more simply and quickly performed in comparison with the comparative example in which the beam orbit is corrected on a trial-and-error basis while manually changing the kick amounts of the steering magnets. The inventors conducted experiments for confirming the correction accuracy by using an experimental system having the same structure and size as those of the particle therapy system of the above-described embodiment. As a result, it was confirmed that, although the error of the beam 1 irradiated from the irradiation nozzle 70 was about several millimeters at maximum before the correction, the error was reduced down to about several tens millimeters at maximum after the correction, i.e., to about $\frac{1}{10}$.

Particularly, in the rotating irradiation facility 103 of the above-described embodiment, the rotating gantry is rotated over a wide range (e.g., range of ±180 degrees) and its rotational angle is finely set (in units of, e.g., 5 degrees). Because the amounts of flexures of the various components caused by their own weights differ depending on the rotational angle, the first and second correction kick amounts must be determined for each value of the rotational angle. With the embodiment, the adjusting time for each value of the rotational angle can be greatly reduced as described above. In addition, because the first and second correction kick amounts are stored in steps 90 and 210 of FIG. 4 described above, the adjusting operation itself can be dispensed with for an angle value, which has been once used in the past, by calling the stored correction data of the steering magnets corresponding to the required energy and rotational angle based on the patient data in the treatment process and then performing the orbit correction without computing the first and second correction kick amounts whenever the orbit correction is performed at a certain angle. It is hence possible to greatly cut down the burden imposed on the operator (doctor or engineer), and to improve convenience to a large extent.

Further, since the steering magnet controller 202 controls respective excitation currents supplied to the steering magnets 181 to 184 provided in the second beam transport system 102B in accordance with the detected signals from the beam position monitors 61 to 64 provided in the second beam transport system 102B, the position of the charged-particle beam can be aligned with the setting position (e.g., the center position) at an inlet of the irradiation facility 103, i.e., at an inlet of the first beam transport system 102A positioned at the center of rotation. Even with changes in the amounts of flexures and deformations of the components of the irradiation facility 103, therefore, the position of the charged-particle beam can be more precisely aligned with the setting position at an outlet of the irradiation nozzle 70 under control of the steering magnets 181 to 184 provided in the first beam transport system 102A.

Moreover, in the irradiation facility 103, since the beam position monitors 61 to 64 are arranged downstream of the magnet that is positioned on the most downstream side in the first beam transport system 102A, the position of the charged-particle beam can be detected by the beam position monitors with high accuracy. This increases the alignment accuracy of the charged-particle beam under control of the excitation currents of, the steering magnets by using the detected signals from the beam position monitors. Also, in the second beam transport system 102B, since the beam position monitors 61 to 64 are arranged downstream of the magnet that is positioned on the most downstream side in the second beam transport system 102B, the position of the charged-particle beam can be detected by the beam position monitors in the second beam transport system 102B with high accuracy. This increases the accuracy in alignment control of the charged-particle beam at the inlet of the first beam transport system 102A.

Furthermore, since the position of the charged-particle beam is detected with the beam position monitors 61, 62 arranged in the irradiation facility 103 upstream of the second scatterer 5, the charged-particle beam can be caused to pass the predetermined position of the second scatterer 5 with the alignment control of the charged-particle beam, and an intensity distribution of the charged-particle beam after passing the second scatterer 5 can be made flat in a direction perpendicular to the direction of beam propagation.

Additionally, the above-described embodiment may be modified such that an x-directional beam scanning magnet and a y-directional beam scanning magnet are provided instead of the second scatterer 5 within the irradiation nozzle 70, and the first scatterer 4 is arranged downstream of those scanning magnets. In this case, the beam position monitors 61, 62 are arranged in the irradiation facility 103 upstream of both the x-directional beam scanning magnet and the y-directional beam scanning magnet. With such a modification, the position of the charged-particle beam incident upon the beam scanning magnets can be controlled with high accuracy, and therefore the position of the charged-particle beam after scanning by the beam scanning magnets can be aligned with the predetermined position. In the case of scanning charged particles, no scatterers are arranged downstream of the x-directional beam scanning magnet and the y-directional beam scanning magnet. Also, in that case, the beam position monitors 61, 62 are arranged upstream of the beam scanning magnets.

A second embodiment of the present invention will be described with reference to FIG. 6. In this second embodiment, the beam orbit correction can be further simplified by utilizing a phase difference of betatron oscillation.

Figure 6:
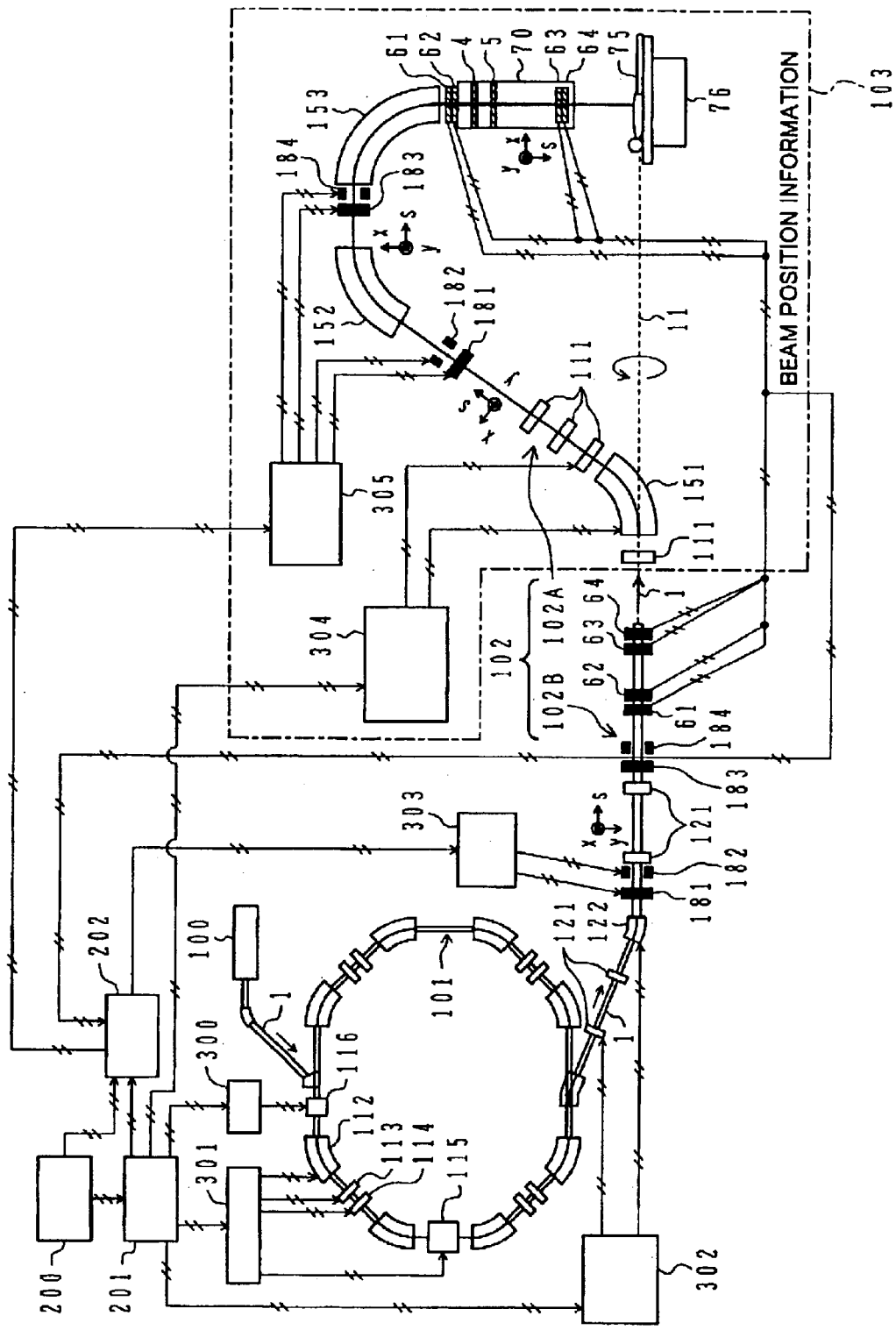
FIG. 6 is a system block diagram showing the overall construction of a particle therapy system according to a second embodiment of the present invention.

FIG. 6 is a system block diagram showing the overall construction of a particle therapy system according to this second embodiment. To avoid complication of the drawing, a flow of part of signals is not shown as in FIG. 1.

A description is now made of the principles of this second embodiment, which differ from those of the above first embodiment.

Generally, as stated in, e.g., OHO' 94 "Fundamentals of Beam Dynamics in Electron Storage Ring", page I-44, a transfer matrix between two A and B points in a particle design orbit can be expressed as given below using Twiss Parameters at each point:

$$M = \begin{pmatrix} \sqrt{\dfrac{\beta_b}{\beta_a}}(\cos\Delta\psi + \alpha_a\sin\Delta\psi) & \sqrt{\beta_a\beta_b}\sin\Delta\psi \\ -\dfrac{1+\alpha_a\alpha_b}{\sqrt{\beta_a\beta_b}}\sin\Delta\psi + \dfrac{\alpha_a-\alpha_b}{\sqrt{\beta_a\beta_b}}\cos\Delta\psi & \sqrt{\dfrac{\beta_a}{\beta_b}}(\cos\Delta\psi - \alpha_b\sin\Delta\psi) \end{pmatrix} \quad (3\text{-}1)$$

In the above formula (3-1), $\beta$ represents a betatron function, $\alpha$ represents an amount defined by $\alpha = -(\frac{1}{2}) \times d\beta/ds$ with s being a coordinate value along the beam design orbit, an affix a represents a value of the point A, and an affix b represents a value of the point B. Also, $\Delta\psi$ represents a phase difference of betatron oscillation propagating from the point A to B.

Based on application of the basic principles, it is assumed that the phase difference of the betatron oscillation from a first steering magnet to a first beam position monitor is $\Delta\psi_1$, and the phase difference of the betatron oscillation from a second steering magnet to the first beam position monitor is $\Delta\psi_2$. Further, the Twiss Parameters $\alpha$, $\beta$ are assumed such that values at the position of the first steering magnet are $\alpha_1$, $\beta_1$, values at the position of the second steering magnet are $\alpha_2$, $\beta_2$, and values at the first beam position monitor are $\alpha_m$, $\beta_m$. From the above assumptions, a transition matrix $M_1$ from the first steering magnet to the first beam position monitor and a transition matrix $M_2$ from the second steering magnet to the first beam position monitor are expressed as give below using the above-mentioned formula (3-1):

$$M_1 = \begin{pmatrix} \sqrt{\dfrac{\beta_m}{\beta_1}}(\cos\Delta\psi_1 + \alpha_1\sin\Delta\psi_1) & \sqrt{\beta_a\beta_b}\sin\Delta\psi_1 \\ -\dfrac{1+\alpha_1\alpha_m}{\sqrt{\beta_1\beta_m}}\sin\Delta\psi_1 + \dfrac{\alpha_1-\alpha_m}{\sqrt{\beta_1\beta_m}}\cos\Delta\psi_1 & \sqrt{\dfrac{\beta_1}{\beta_m}}(\cos\Delta\psi_1 - \alpha_m\sin\Delta\psi_1) \end{pmatrix} \quad (3\text{-}2)$$

$$M_2 = \begin{pmatrix} \sqrt{\dfrac{\beta_m}{\beta_2}}(\cos\Delta\psi_2 + \alpha_2\sin\Delta\psi_2) & \sqrt{\beta_2\beta_m}\sin\Delta\psi_2 \\ -\dfrac{1+\alpha_2\alpha_m}{\sqrt{\beta_2\beta_m}}\sin\Delta\psi_2 + \dfrac{\alpha_2-\alpha_m}{\sqrt{\beta_2\beta_m}}\cos\Delta\psi_2 & \sqrt{\dfrac{\beta_2}{\beta_m}}(\cos\Delta\psi_2 - \alpha_m\sin\Delta\psi_2) \end{pmatrix} \quad (3\text{-}3)$$

Assuming here that the phase difference from the first steering magnet to the first beam position monitor is $180°+180°\times m$ (m=0, 1, 2, ...), the phase difference from the second steering magnet to the first beam position monitor is $90°+180\times n$ (n=0, 1, 2, ...), and the beam spread at the first beam position monitor is parallel ($\alpha_m=0$), the above formulae (3-2) and (3-3) can be rewritten to the following ones (3-4) and (3-5), respectively:

$$M_1 = \begin{pmatrix} (-1)^{m+1}\sqrt{\dfrac{\beta_m}{\beta_1}} & 0 \\ (-1)^{m+1}\dfrac{\alpha_1}{\sqrt{\beta_1\beta_m}} & (-1)^{m+1}\sqrt{\dfrac{\beta_1}{\beta_m}} \end{pmatrix} \quad (3\text{-}4)$$

$$M_2 = \begin{pmatrix} (-1)^n\alpha_2\sqrt{\dfrac{\beta_m}{\beta_2}} & (-1)^n\sqrt{\beta_2\beta_m} \\ (-1)^{n+1}\dfrac{1}{\sqrt{\beta_2\beta_m}} & 0 \end{pmatrix} \quad (3\text{-}5)$$

Here, since the correction kick amounts are determined by solving the formula (2-8) in the above-described first embodiment, namely:

$$\begin{pmatrix} a_1 & b_1 \\ c_1 & d_1 \end{pmatrix}\begin{pmatrix} 0 \\ k_1 \end{pmatrix} + \begin{pmatrix} a_2 & b_2 \\ c_2 & d_2 \end{pmatrix}\begin{pmatrix} 0 \\ k_2 \end{pmatrix} + \begin{pmatrix} x_{err} \\ x'_{err} \end{pmatrix} =$$

$$\begin{pmatrix} b_1 & b_2 \\ d_1 & d_2 \end{pmatrix}\begin{pmatrix} k_1 \\ k_2 \end{pmatrix} + \begin{pmatrix} x_{err} \\ x'_{err} \end{pmatrix} = \begin{pmatrix} 0 \\ 0 \end{pmatrix}$$

they are obtained as given below by putting the formulae (3-4) and (3-5) in the formula (2-8):

$$k_1 = (-1)^m \sqrt{\dfrac{\beta_m}{\beta_1}} x'_{err} \quad (3\text{-}6)$$

$$k_2 = (-1)^{n+1} \dfrac{x_{err}}{\sqrt{\beta_2\beta_m}} \quad (3\text{-}7)$$

In other words, the kick amount of the first steering magnet is able to independently correct only the error of the orbit gradient in the irradiation nozzle as indicated in the formulae (3-6), and to independently correct only the error of the orbit displacement in the irradiation nozzle as indicated in the formulae (3-7). Hence, the correcting operation is further simplified.

On the basis of the principles described above, in this embodiment, an x-direction first steering magnet 181 is arranged in a bending plane (x-direction) of the rotating irradiation facility 103 at a position having a phase difference of 180 degrees from an x-direction first beam position monitor 61, and an x-direction second steering magnet 183 is arranged therein at a position having a phase difference of 90 degrees from the x-direction first beam position monitor 61, as shown in FIG. 6 (correspondingly, a second bending magnet 152 is arranged between the first steering magnet 181 and the second steering magnet 182, and a third steering magnet 153 is added). The magnetic field gradients of quadrupole magnets 111, which satisfy the above-described conditions for the phase difference and $\alpha_m=0$ at the x-direction first beam position monitor 61 are determined in the stage of optical design of the irradiation facility 103 beforehand. By exciting the quadrupole magnets 111 so as to provide the magnetic field gradients based on the optical design, the orbit correction in the x-direction can be even more simply performed than the first embodiment.

A third embodiment of the present invention will be described with reference to FIG. 7. This third embodiment employs steering magnets having different functions from those used in the above embodiment.

Figure 7:
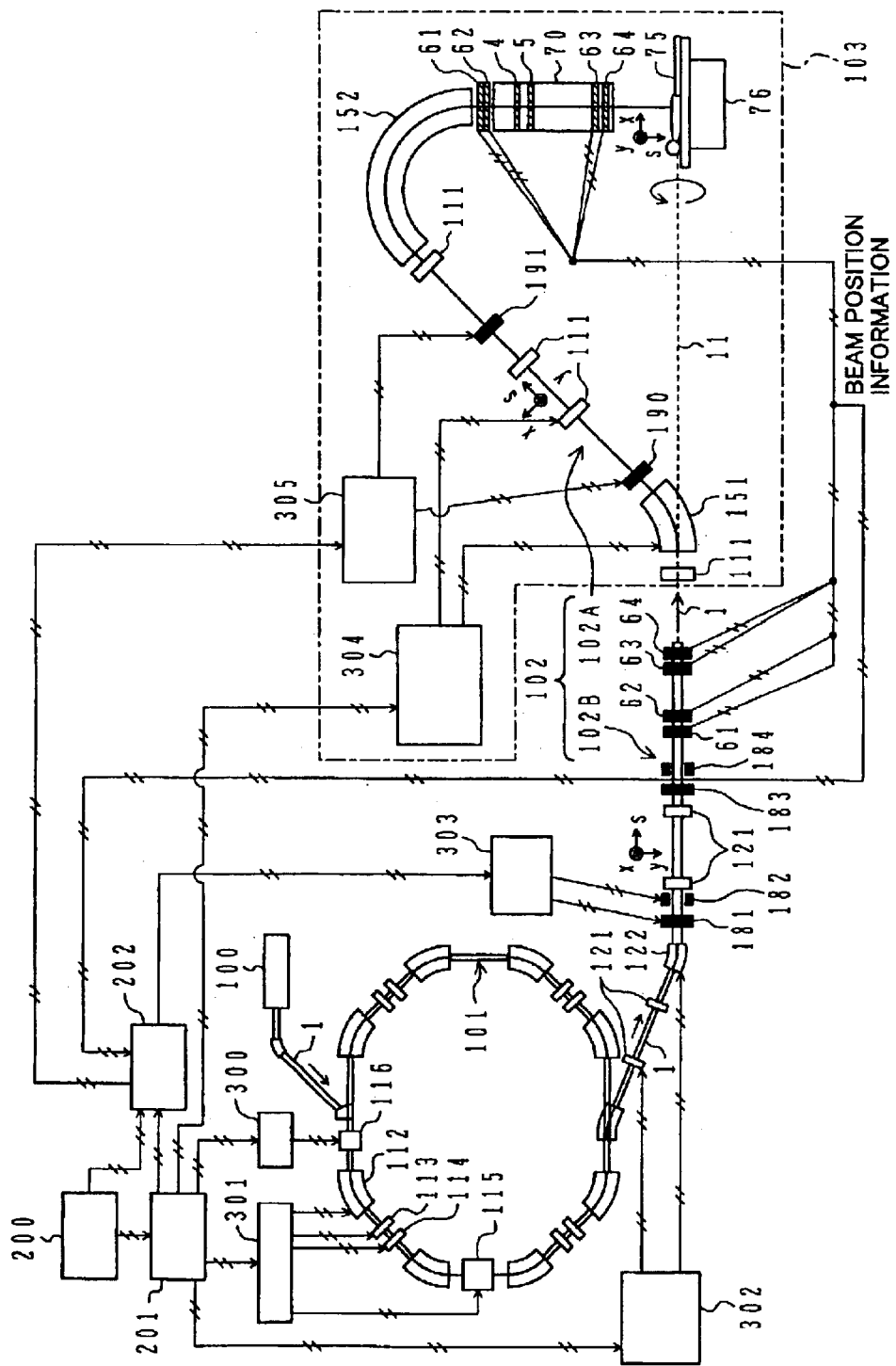
FIG. 7 is a system block diagram showing the overall construction of a particle therapy system according to a third embodiment of the present invention.

FIG. 7 is a system block diagram showing the overall construction of a particle therapy system according to this third embodiment. To avoid complication of the drawing, a flow of part of signals is not shown as in FIGS. 1 and 6.

In the particle therapy system of this embodiment, as shown in FIG. 7, a single first x-y direction steering magnet 190 is provided in place of the first x-direction steering magnet 181 and the first y-direction steering magnet 182 in the first beam transport system 102A of the first embodiment shown in FIG. 1, and a single second x-y direction steering magnet 191 is provided in place of the second x-direction steering magnet 183 and the second y-direction steering magnet 184.

Employing the x-y direction steering magnets 190, 191 is effective in reducing a space necessary for equipment installation, and especially in contributing a reduction in the size of the rotating irradiation facility 103.

A fourth embodiment of the present invention will be described with reference to FIG. 8. In this fourth embodiment, the present invention is applied to only the side of the rotating gantry.

Figure 8:
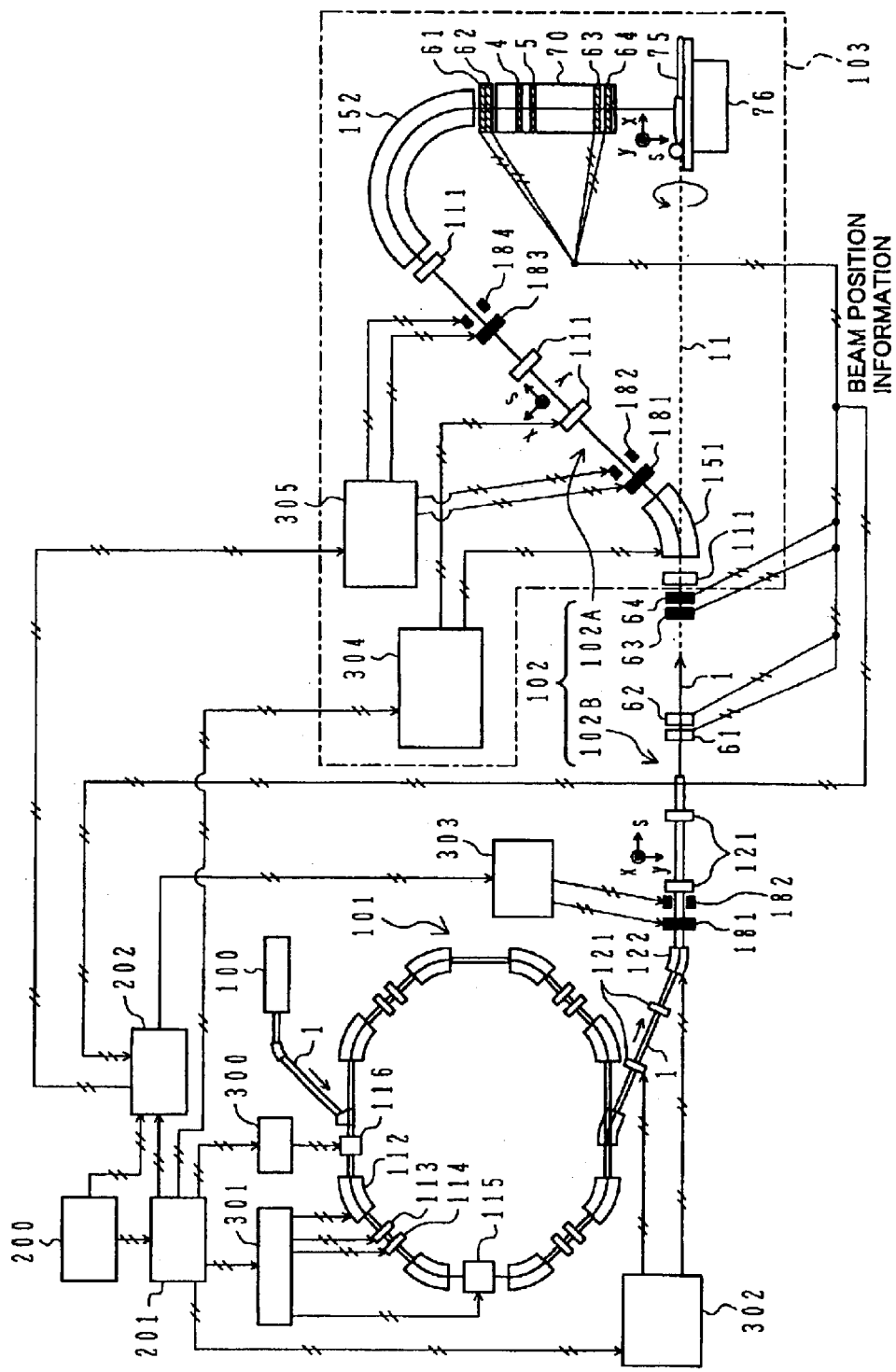
FIG. 8 is a system block diagram showing the overall construction of a particle therapy system according to a fourth embodiment of the present invention.

FIG. 8 is a system block diagram showing the overall construction of a particle therapy system according to this fourth embodiment. To avoid complication of the drawing, a flow of part of signals is not shown as in FIGS. 1, 6 and 7.

As shown in FIG. 8, the particle therapy system of this embodiment is constructed by omitting the second steering magnets 183, 184 provided in the second beam transport system 102B from the construction of the first embodiment.

Stated otherwise, in this fourth embodiment, the orbit correction of the beam 1 is performed by correcting the beam orbit in the second beam transport system 102B with the manual adjustment on a trial-and-error basis as conventional, and by applying the present invention to only the rotating gantry side and correcting the beam orbit based on the approximation models.

More specifically, of the control flow in the first embodiment shown in FIG. 4, the processing corresponding to steps 10 to 90 is not performed in this fourth embodiment, and the beam orbit is corrected with the manual adjustment on a trial-and-error basis in accordance with a sequence of steps 300 to 320 shown in FIG. 5 by using the first steering magnets 181, 182 provided in the second beam transport system 102B.

After correcting the beam orbit on the side of the second beam transport system 102B in such a way, the beam orbit correction on the rotating gantry side is performed through steps 100 to 210, shown in FIG. 4, by employing the first and second steering magnets 181, 182, 183 and 184 provided on the rotating gantry side.

With this fourth embodiment, the above-described advantage of the present invention, i.e., a reduction of labor and time required for the orbit correction, cannot be obtained on the side of the second beam transport system 102B, but it can be obtained on the rotating gantry side. Therefore, the beam orbit correction can be more simply and quickly performed at least from the overall point of view than the conventional method in which the beam orbit is manually adjusted on a trial-and-error basis in both of the second beam transport system 102B side and the rotating gantry side.

Particularly, in the above-described particle therapy system including the rotating irradiation facility, once the beam orbit is corrected, e.g., at the start of treatment, there is no need of repeating the correction thereafter on the side of the second beam transport system 102B. On the rotating gantry side, however, since the correction kick amounts of the steering magnets are also changed whenever the rotational angle changes, more labor and burden are in fact required for the beam orbit correction. In this embodiment, the method of correcting the beam orbit according to the present invention is applied to the rotating gantry side requiring more labor and burden, and hence the adjusting time in the correcting operation can be greatly cut down.

A fifth embodiment of the present invention will be described with reference to FIG. 9. In this fifth embodiment, the construction of the above fourth embodiment is applied to a vertical stationary gantry.

Figure 9:
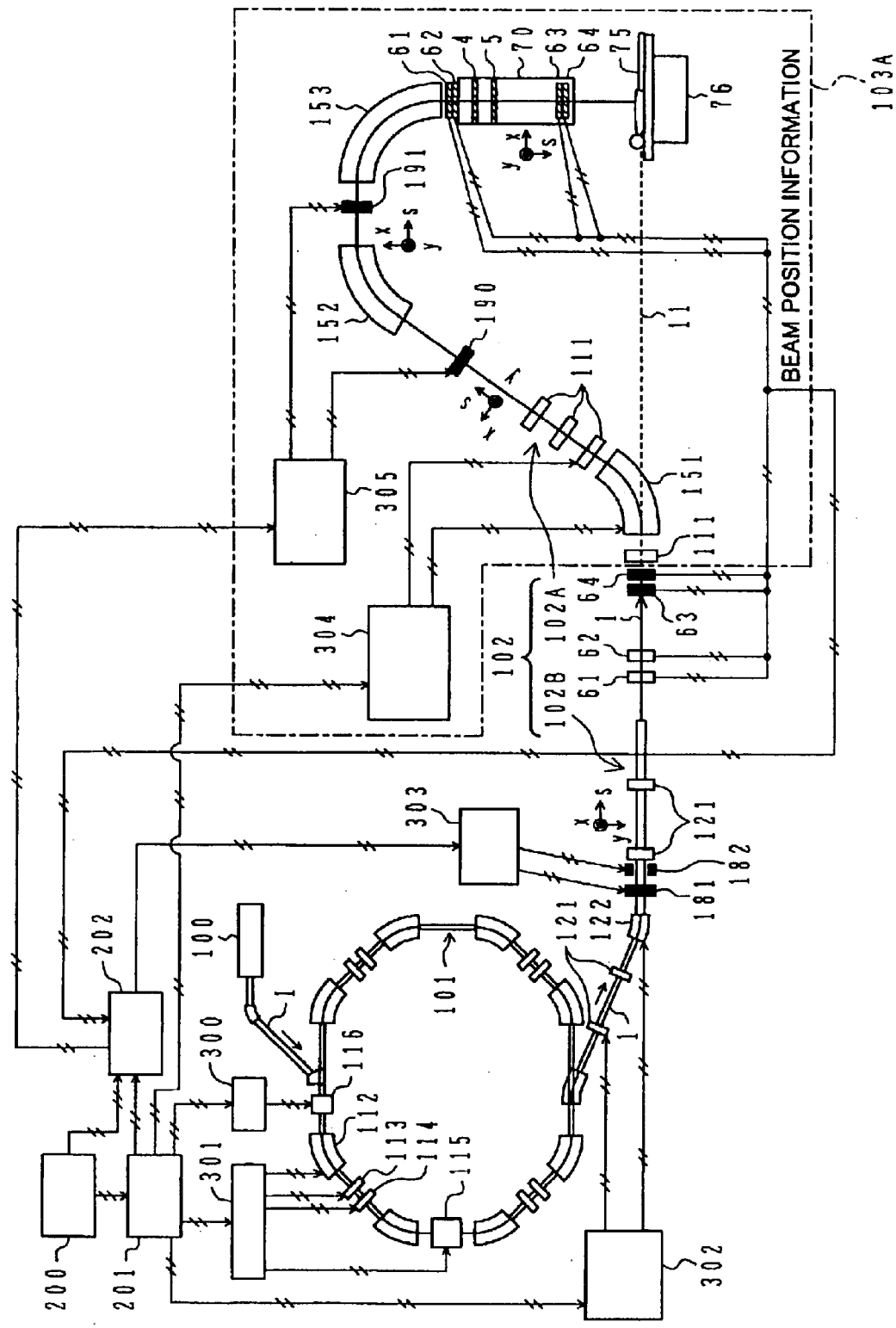
FIG. 9 is a system block diagram showing the overall construction of a particle therapy system according to a fifth embodiment of the present invention.

FIG. 9 is a system block diagram showing the overall construction of a particle therapy system according to this fifth embodiment. To avoid complication of the drawing, a flow of part of signals is not shown as in FIGS. 1 and 6 to 8. The same components as those in FIGS. 7 and 8 are denoted by the same reference symbols and a description thereof is omitted here.

As shown in FIG. 9, the particle therapy system of this embodiment includes a vertical stationary irradiation facility 103A. While the irradiation facility 103A includes a first beam transport system 102A, an irradiation nozzle 70 and a treatment bench (patient bed) 76 as with the irradiation facility 103 in the above first embodiment, this fifth embodiment differs from the fourth embodiment in that those components are not rotated and the beam is always irradiated to a patient 75 from above. Further, as the steering magnets, there are provided a single first x-y direction steering magnet 190 and a single second x-y direction steering magnet 191 similarly to the third embodiment shown in FIG. 7.

This fifth embodiment can also provide, as with the above fourth embodiment, the advantage of reducing labor and time required for the orbit correction on the side of the stationary irradiation facility 103A.

In particular, this fifth embodiment is effective in performing the orbit correction when the orbit of the beam 1 transported to the stationary irradiation facility 103A is changed for some reason, or when new alignment errors are added in the installation place of the irradiation facility because of, e.g., earthquake.

A sixth embodiment of the present invention will be described with reference to FIG. 10. In this sixth embodiment, the construction of the above fourth embodiment is applied to a horizontal stationary gantry.

Figure 10:
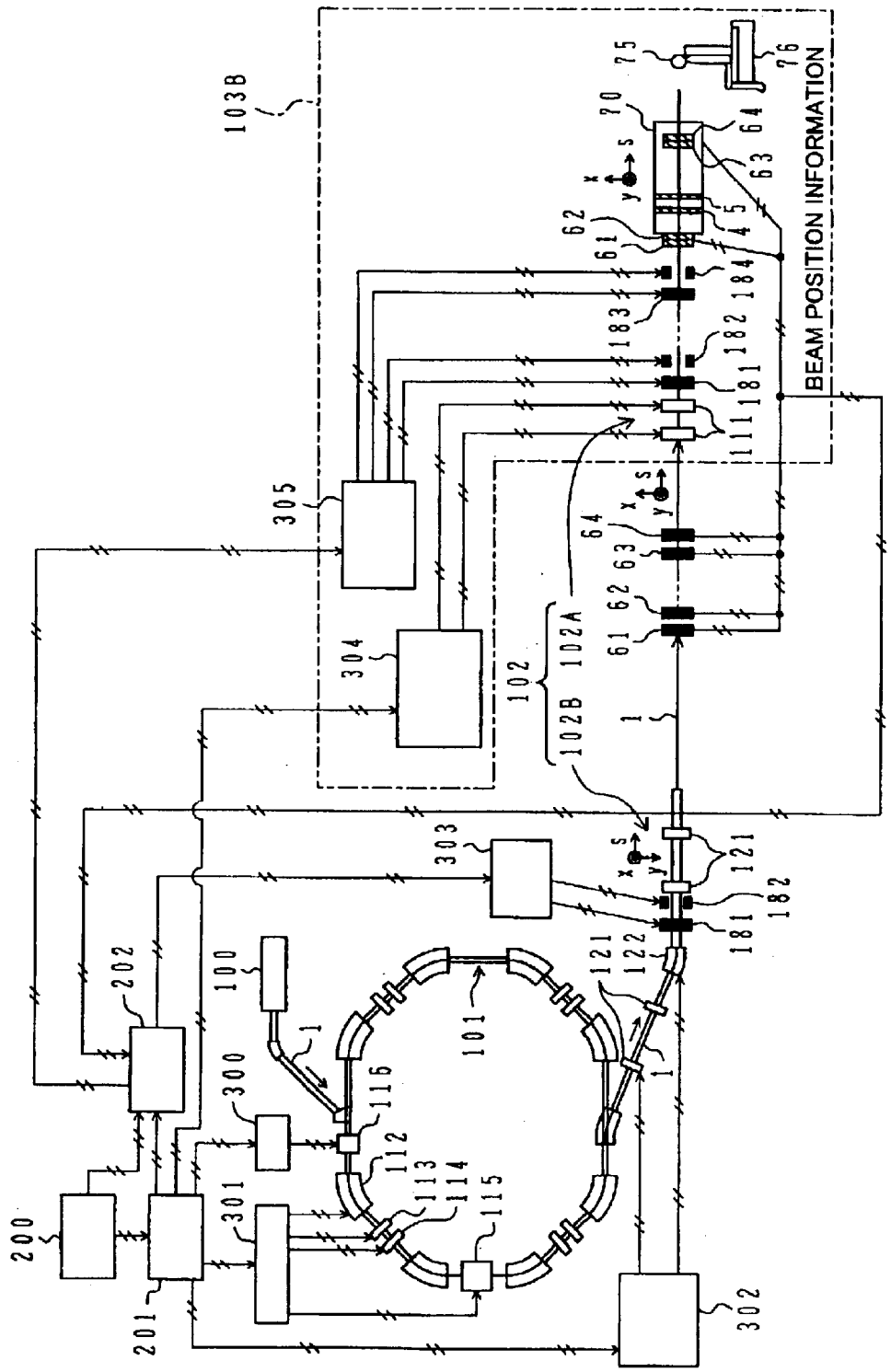
FIG. 10 is a system block diagram showing the overall construction of a particle therapy system according to a sixth embodiment of the present invention.

FIG. 10 is a system block diagram showing the overall construction of a particle therapy system according to this sixth embodiment. To avoid complication of the drawing, a flow of part of signals is not shown as in FIGS. 1 and 6 to 9. The same components as those in drawings described above are denoted by the same reference symbols and a description thereof is omitted here.

As shown in FIG. 10, the particle therapy system of this embodiment includes a horizontal stationary irradiation facility 103B. While the irradiation facility 103B includes a first beam transport system 102A, an irradiation nozzle 70 and a treatment bench (patient bed) 76 having the same functions as the corresponding components in each of the above embodiments, this sixth embodiment differs from the above embodiments in that those components are not rotated and the beam is always irradiated to a patient 75 in the horizontal direction.

This sixth embodiment can also provide, as with the above fifth embodiment, the advantage of reducing labor and time required for the orbit correction on the side of the stationary irradiation facility 103B.

A seventh embodiment of the present invention will be described with reference to FIG. 11. In this seventh embodiment, the present invention is applied to only the second beam transport system 102B contrary to the above fourth embodiment.

Figure 11:
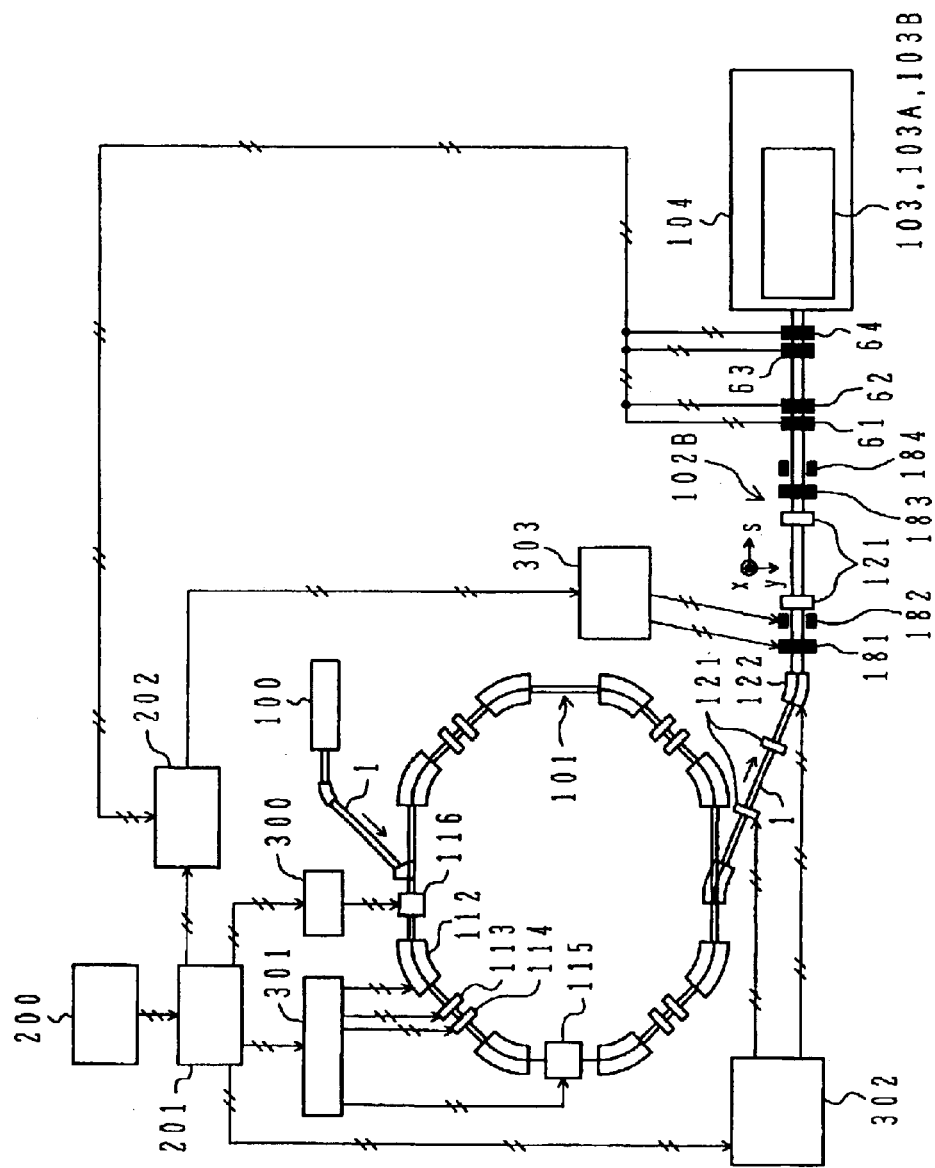
FIG. 11 is a system block diagram showing the overall construction of a particle therapy system according to a seventh embodiment of the present invention.

FIG. 11 is a system block diagram showing the overall construction of a particle therapy system according to this seventh embodiment. To avoid complication of the drawing, a flow of part of signals is not shown as in FIGS. 1 and 6 to 10. The same components as those in the drawings described above are denoted by the same reference symbols and a description thereof is omitted here.

As shown in FIG. 11, the particle therapy system of this embodiment includes one of a rotating irradiation facility 103, a vertical stationary irradiation facility 103A, and a horizontal stationary irradiation facility 103B.

In this seventh embodiment, the orbit correction of the beam 1 is performed by correcting the beam orbit on the side of the irradiation facility 103, 103A or 103B with the manual adjustment on a trial-and-error basis as conventional, and by applying the present invention to only the second beam transport system 102B and correcting the beam orbit based on the approximation models.

More specifically, the beam orbit correction is first performed through steps 10 to 90 of the control flow in the first embodiment, shown in FIG. 4, by employing the first and second steering magnets 181, 182, 183 and 184 provided on side of the second beam transport system 102B.

Then, of the control flow in the first embodiment shown in FIG. 4, the processing corresponding to steps 100 to 210 is not performed in this seventh embodiment, and the beam orbit is corrected with the manual adjustment on a trial-and-error basis in accordance with a sequence of steps 300 to 320 shown in FIG. 5 by using the steering magnets provided on the side of the irradiation facility 103, 103A or 103B.

With this seventh embodiment, the above-described advantage of the present invention, i.e., a reduction of labor and time required for the orbit correction, cannot be obtained on the side of the irradiation facility 103, 103A or 103B, but it can be obtained on the side of the second beam transport system 102B. Therefore, the beam orbit correction can be more simply and quickly performed at least from the overall point of view than the conventional method in which the beam orbit is manually adjusted on a trial-and-error basis in both of the second transport system 102B side and the irradiation facility side.

Figure 12:
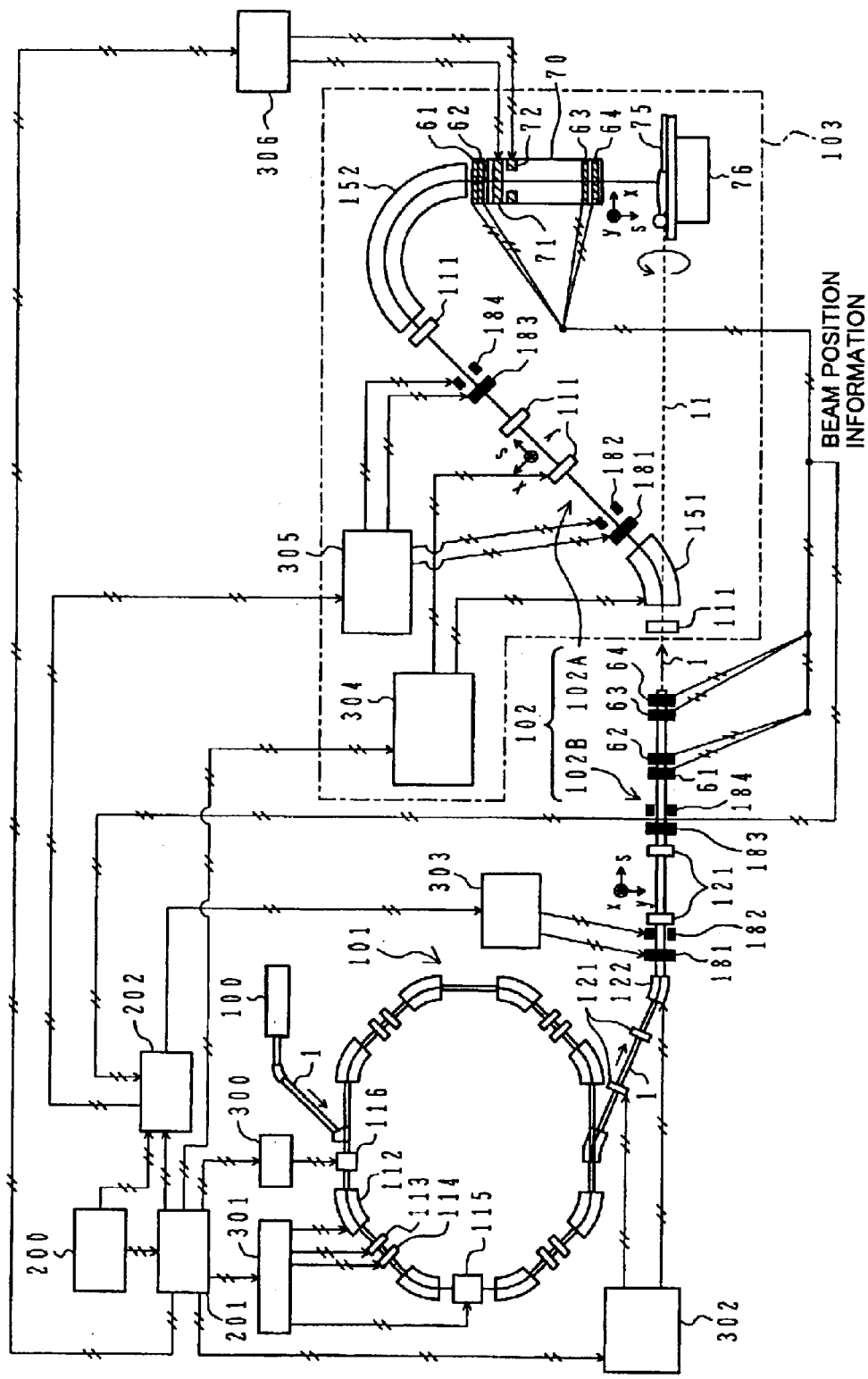
FIG. 12 is a system block diagram showing the overall construction of a particle therapy system according to an eighth embodiment of the present invention.

An eighth embodiment of the present invention will be described with reference to FIG. 12. In this eighth embodiment, the present invention is applied to the case in which a beam scanning method is employed as the method of forming an irradiation field.

More specifically, in order to carry out the beam scanning method, an x-direction beam scanning magnet 71 and a y-direction beam scanning magnet 72 are disposed downstream of the x-direction first beam position monitor 61 and the y-direction first beam position monitor 62 in an irradiation field forming nozzle (irradiation nozzle) 70.

The beam orbit correction using the beam scanning method is performed in a similar manner to that in the first embodiment so that the beam orbit as a reference, which is resulted when the beam is not scanned, coincides with the design orbit in the irradiation nozzle 70. After the orbit correction, the irradiation for treatment is performed by controlling current values supplied from a power supply unit 306 for the scanning magnets to the x-direction beam scanning magnet 71 and the y-direction beam scanning magnet 72 in accordance with an instruction from the accelerator controller 201 depending on the position of the diseased area, and by scanning the beam 1 in the x-direction and the y-direction.

In all of the embodiments described above, the main accelerator 101 may be constituted as a cyclotron in place of a synchrotron. In the case of employing a cyclotron, the pre-stage accelerator 100 is not required. A particle therapy system using such a cyclotron can also provide the advantage obtainable with corresponding one of the above-described embodiments.

As described hereinabove, with the present invention according to one aspect, a first displacement amount computing unit determines respective first displacement amounts, by which a position of a charged-particle beam is to be displaced by first and second steering magnets, in accordance with detected signals outputted from first and second beam position detecting units, and a first control unit controls respective excitation currents of the first and second steering magnets in accordance with the respective first displacement amounts, whereby the position of the charged-particle beam can be displaced, as required, to come within a set range. Consequently, the orbit correction can be more simply and quickly performed, while greatly reducing the required labor and time, as compared with the conventional system.

With the present invention according to another aspect, a second displacement amount computing unit determines respective second displacement amounts, by which a position of a charged-particle beam is to be displaced by first and second steering magnets, in accordance with detected signals outputted from third and fourth beam position detecting units, and a second control unit controls respective excitation currents of the third and fourth steering magnets in accordance with the respective second displacement amounts, whereby the position of the charged-particle beam can be displaced, as required, to come within a set range. Consequently, the orbit correction can be more simply and quickly performed, while greatly reducing the required labor and time, as compared with the conventional system.

What is claimed is:

1. A particle therapy system comprising an accelerator for accelerating a charged-particle beam to a set level of energy, and a rotating irradiation facility for irradiating the charged-particle beam extracted from said accelerator, said irradiation facility comprising first beam transport appratus for transporting the charged-particle beam extracted from said accelerator, and irradiation field forming appratus for forming an irradiation field of the charged-particle beam transported by said first beam transport appratus, wherein said particle therapy system further comprises:

first beam position detecting appratus arranged along an orbit of the charged-particle beam downstream of a most downstream one of magnets provided in said first beam transport appratus, and detecting a position at which the charged-particle beam passes;

second beam position detecting appratus arranged along the orbit of the charged-particle beam downstream of said first beam position detecting appratus, and detecting a position at which the charged-particle beam passes;

a first steering magnet and a second steering magnet both provided in said first beam transport appratus upstream of said first beam position detecting appratus;

first displacement amount computing appratus for determining respective first displacement amounts, by which the position of the charged-particle beam is to be displaced by said first and second steering magnets, in accordance with detected signals outputted from said first and second beam position detecting appratus; and first cotrol system for controlling respective excitation currents of said first and second steering magnets in accordance with the respective first displacement amounts.

2. A particle therapy system according to claim 1, wherein said irradiation field forming appratus includes a first scatterer and a second scatterer arranged downstream of said first scatterer, and said first beam position detecting appratus is arranged upstream of said second scatterer.

3. A particle therapy system according to claim 2, wherein said first displacement amount computing appratus determines the first displacement amounts in accordance with the detected signals outputted from said first and second beam position detecting appratus so that the position of the charged-particle beam comes within a set orbit in said irradiation field forming appratus.

4. A particle therapy system according to claim 1, wherein said irradiation field forming appratus includes beam scanning appratus for scanning the charged-particle beam, and said first beam position detecting appratus is arranged upstream of said beam scanning appratus.

5. A particle therapy system according to claim 4, wherein said first displacement amount computing appratus determines the first displacement amounts in accordance with the detected signals outputted from said first and second beam position detecting appratus so that the position of the charged-particle beam comes within a set orbit in said irradiation field forming appratus.

6. A particle therapy system according to claim 5, wherein said first displacement amount computing apparatus determines the first displacement amounts on the basis of approximation models using a plurality of transfer matrices representing respective transport characteristics of various transport elements of said first beam transport apparatus, which include at least said first and second steering magnets.

7. A particle therapy system according to claim 1, wherein said first displacement amount computing appratus determines the first displacement amounts in accordance with the detected signals outputted from said first and second beam position detecting appratus so that the position of the charged-particle beam comes within a set orbit in said irradiation field forming appratus.

8. A particle therapy system according to claim 7, wherein at least one of said first and second steering magnets displace the charged-particle beam in one direction and displace the charged-particle beam in an other direction perpendicular to the one direction.

9. A particle therapy system according to claim 1, wherein said first displacement amount computing apparatus determines the first displacement amounts on the basis of approximation models using a plurality of transfer matrices representing respective transport characteristics of various transport elements of said first beam transport apparatus, which include at least said first and second steering magnets.

10. A particle therapy system according to claim 1, wherein at least one of said first and second steering magnets displace the charged-particle beam in one direction and displace the charged-particle beam in an other direction perpendicular to the one direction.

11. A particle therapy system according to claim 10, wherein said second displacement amount computing apparatus determines the second displacement amounts on the basis of approximation models using a plurality of transfer matrices representing respective transport characteristics of various transport elements of said second beam transport apparatus, which include at least said third and fourth steering magnets.

12. A particle therapy system comprising an accelerator for accelerating a charged-particle beam to a set level of energy, a rotating irradiation facility for irradiating the charged-particle beam extracted from said accelerator, and second beam transport apparatus for transporting the charged-particle beam extracted from said accelerator to said irradiation facility, wherein said particle therapy system further comprises:

third beam position detecting apparatus for detecting a position in said second beam transport beam transport apparatus at which the charged-particle beam passes;

fourth beam position detecting apparatus for detecting, downstream of said third beam position detecting apparatus, a position in said second beam transport apparatus at which the charged-particle beam passes;

a third steering magnet and a fourth steering magnet both provided in said second beam transport apparatus upstream of said third beam position detecting apparatus;

second displacement amount computing apparatus for determining second displacement amounts, by which the position of the charged-particle beam is to be displaced by said third and fourth steering magnets, in accordance with detected signals outputted from said third and fourth beam position detecting apparatus; and second control system for controlling respective excitation currents of said third and fourth steering magnets in accordance with the respective second displacement amounts.

13. A particle therapy system according to claim 12, wherein said second displacement amount computing apparatus determines the second displacement amounts in accordance with the detected signals outputted from said third and fourth beam position detecting apparatus so that the position of the charged-particle beam comes within a set orbit in said irradiation field forming apparatus.

14. A particle therapy system according to claim 13, wherein said second displacement amount computing apparatus determines the second displacement amounts on the basis of approximation models using a plurality of transfer matrices representing respective transport characteristics of various transport elements of said second beam transport apparatus, which include at least said third and fourth steering magnets.

15. A particle therapy system according to any one of claim 12, wherein at least one of said third and fourth steering magnets displace the charged-particle beam in one direction and displace the charged-particle beam in an other direction perpendicular to the one direction.

16. A particle therapy system according to any one of claim 13, wherein at least one of said third and fourth steering magnets displace the charged-particle beam in one direction and displace the charged-particle beam in an other direction perpendicular to the one direction.

17. A particle therapy system comprising an accelerator for accelerating a charged-particle beam to a set level of energy, a stationary irradiation facility for irradiating the charged-particle beam, and beam transport apparatus for transporting the charged-particle beam extracted from said accelerator to said irradiation facility, wherein said particle therapy system further comprises:

first beam position detecting apparatus arranged along an orbit of the charged-particle beam downstream of a most downstream one of magnets provided in said beam transport apparatus, and detecting a position at which the charged-particle beam passes;

second beam position detecting apparatus arranged along the orbit of the charged-particle beam downstream of said first beam position detecting apparatus, and detecting a position at which the charged-particle beam passes;

a first steering magnet and a second steering magnet both provided in said beam transport apparatus upstream of said first beam position detecting apparatus;

first displacement amount computing apparatus for determining respective first displacement amounts, by which the position of the charged-particle beam is to be displaced by said first and second steering magnets, in accordance with detected signals outputted from said first and second beam position detecting apparatus; and first cotrol system for controlling respective excitation currents of said first and second steering magnets in accordance with the respective first displacement amounts.

18. A particle therapy system according to claim 17, wherein said irradiation facility includes a first scatterer and a second scatterer arranged downstream of said first scatterer, and said first beam position detecting apparatus is arranged upstream of said second scatterer.

19. A particle therapy system according to claim 17, wherein said irradiation facility includes beam scanning apparatus for scanning the charged-particle beam, and said first beam position detecting apparatus is arranged upstream of said beam scanning apparatus.

* * * * *